US012575845B2

(12) United States Patent
Arad Hadar et al.

(10) Patent No.: US 12,575,845 B2
(45) **Date of Patent: \*Mar. 17, 2026**

(54) THROMBECTOMY DEVICE, SYSTEM AND METHOD FOR EXTRACTION OF VASCULAR THROMBI FROM A BLOOD VESSEL

(71) Applicant: Anaconda Biomed, S.L., Barcelona (ES)

(72) Inventors: Ofir Arad Hadar, Barcelona (ES); Aaron Vilalta Costa, Girona (ES)

(73) Assignee: Anaconda Biomed, S.L., Barcelona (ES)

( \* ) Notice: Subject to any disclaimer, the term of this patent is extended or adjusted under 35 U.S.C. 154(b) by 470 days.

This patent is subject to a terminal disclaimer.

(21) Appl. No.: 18/145,386

(22) Filed: Dec. 22, 2022

(65) Prior Publication Data

US 2023/0127145 A1      Apr. 27, 2023

Related U.S. Application Data

(63) Continuation-in-part of application No. 17/235,764, filed on Apr. 20, 2021, now Pat. No. 12,161,352, (Continued)

(51) Int. Cl.
    *A61B 17/22*        (2006.01)
    *A61B 17/00*        (2006.01)
    (Continued)

(52) U.S. Cl.
    CPC .. *A61B 17/22031* (2013.01); *A61B 17/12031* (2013.01); *A61B 17/12109* (2013.01);
    (Continued)

(58) Field of Classification Search
    CPC .......... A61B 17/12022; A61B 17/1204; A61B 17/12109; A61B 17/12131;
    (Continued)

(56) References Cited

U.S. PATENT DOCUMENTS 4,574,176 A      3/1986  Sharp
4,794,231 A      12/1988 Banas et al.
    (Continued)

FOREIGN PATENT DOCUMENTS

AU      2018274903 B2    4/2020
CN      102973332 A      3/2013
    (Continued)

OTHER PUBLICATIONS

Medtronic; Medtronic.com; The Solitaire Platinum Revascularization Device; Model Specifications; DC00079632 Rev A ; 1 page; retrived from the internet (https//www.medtronic.com) on Mar. 2018.

(Continued)

*Primary Examiner* — Kankindi Rwego
(74) *Attorney, Agent, or Firm* — Shay Glenn LLP

(57)      ABSTRACT

Thrombectomy devices, systems and methods for extraction of vascular thrombi from a blood vessel.

20 Claims, 9 Drawing Sheets

Related U.S. Application Data which is a continuation of application No. 15/649,266, filed on Jul. 13, 2017, now Pat. No. 11,013,523, which is a continuation-in-part of application No. PCT/EP2015/079400, filed on Dec. 11, 2015, application No. 18/145,386 is a continuation-in-part of application No. 17/500,844, filed on Oct. 13, 2021, now Pat. No. 11,771,446, and a continuation-in-part of application No. 17/274,973, filed on Mar. 10, 2021, now Pat. No. 11,986,195, and a continuation-in-part of application No. 17/291,696, filed on May 6, 2021.

(60) Provisional application No. 63/093,540, filed on Oct. 19, 2020.

(51) Int. Cl.

| *A61B 17/12* | (2006.01) |
|---|---|
| *A61B 17/221* | (2006.01) |
| *A61M 29/00* | (2006.01) |
| *A61B 90/00* | (2016.01) |

(52) U.S. Cl.

CPC ...... *A61B 17/12136* (2013.01); *A61B 17/221* (2013.01); *A61M 29/00* (2013.01); *A61B 2017/00867* (2013.01); *A61B 2017/00938* (2013.01); *A61B 2017/00942* (2013.01); *A61B 2017/1205* (2013.01); *A61B 2017/22051* (2013.01); *A61B 2017/2215* (2013.01); *A61B 2090/3966* (2016.02); *A61B 2217/007* (2013.01)

(58) Field of Classification Search

CPC ........ A61B 17/12172; A61B 17/12136; A61B 17/22031; A61B 17/22032; A61B 17/221; A61B 17/32002; A61B 2017/0057; A61B 2017/2215; A61B 2017/22051; A61B 2017/00323; A61B 2017/00336; A61B 2017/22094; A61B 2017/2212; A61B 2017/22034; A61B 2017/22035; A61B 2017/2217; A61B 2017/22001; A61B 2017/22002; A61B 2017/22079; A61B 2017/221; A61M 29/00; A61M 29/02; A61M 2029/025; A61M 2205/0272; A61M 25/0067; A61M 25/0074; A61M 2025/0079

See application file for complete search history.

(56) References Cited

U.S. PATENT DOCUMENTS

| | | | |
|---|---|---|---|
| 4,921,478 A | 5/1990 | Solano et al. | |
| 5,011,488 A | 4/1991 | Ginsburg | |
| 5,092,839 A * | 3/1992 | Kipperman | A61M 25/104 606/159 |
| 5,102,415 A | 4/1992 | Guenther et al. | |
| 5,190,561 A | 3/1993 | Graber | |
| 5,234,416 A | 8/1993 | MacCaulay et al. | |
| 5,449,373 A | 9/1995 | Pinchasik et al. | |
| 5,603,705 A | 2/1997 | Berg | |
| 5,605,530 A | 2/1997 | Fishell et al. | |
| 5,769,871 A | 6/1998 | Mers Kelly et al. | |
| 5,908,435 A | 6/1999 | Samuels | |
| 5,971,938 A | 10/1999 | Hart et al. | |
| 5,972,019 A | 10/1999 | Engelson et al. | |
| 6,066,149 A | 5/2000 | Samson et al. | |
| 6,159,230 A | 12/2000 | Samuels | |
| 6,190,303 B1 | 2/2001 | Glenn et al. | |
| 6,402,771 B1 | 6/2002 | Palmer et al. | |
| 6,514,273 B1 | 2/2003 | Voss et al. | |
| 6,663,650 B2 | 12/2003 | Sepetka et al. | |

| | | | |
|---|---|---|---|
| 6,695,858 B1 | 2/2004 | Dubrul et al. | |
| 6,730,104 B1 | 5/2004 | Sepetka et al. | |
| 6,752,819 B1 | 6/2004 | Brady et al. | |
| 7,004,954 B1 | 2/2006 | Voss et al. | |
| 7,108,677 B2 | 9/2006 | Courtney et al. | |
| 7,578,830 B2 | 8/2009 | Kusleika et al. | |
| 7,686,825 B2 | 3/2010 | Hauser et al. | |
| 7,867,272 B2 | 1/2011 | Niermann | |
| 7,993,302 B2 | 8/2011 | Hebert et al. | |
| 8,088,140 B2 | 1/2012 | Ferrera et al. | |
| 8,298,257 B2 | 10/2012 | Sepetka et al. | |
| 8,679,142 B2 | 3/2014 | Slee et al. | |
| 8,758,364 B2 | 6/2014 | Eckhouse et al. | |
| 8,784,441 B2 | 7/2014 | Rosenbluth et al. | |
| 8,858,497 B2 | 10/2014 | Di Palma et al. | |
| 8,864,792 B2 | 10/2014 | Eckhouse et al. | |
| 8,940,003 B2 | 1/2015 | Slee et al. | |
| 8,984,003 B2 | 3/2015 | Ahmed et al. | |
| 9,005,237 B2 | 4/2015 | Eckhouse et al. | |
| 9,034,008 B2 | 5/2015 | Eckhouse et al. | |
| 9,186,487 B2 | 11/2015 | Dubrul et al. | |
| 9,463,035 B1 | 10/2016 | Greenhalgh et al. | |
| 9,561,121 B2 | 2/2017 | Sudin et al. | |
| 9,585,741 B2 | 3/2017 | Ma | |
| 9,700,331 B2 | 7/2017 | Grandfield et al. | |
| 9,844,381 B2 | 12/2017 | Eckhouse et al. | |
| 9,861,783 B2 | 1/2018 | Garrison et al. | |
| 10,285,720 B2 | 5/2019 | Gilvarry et al. | |
| 10,292,804 B2 | 5/2019 | Wang et al. | |
| 10,426,644 B2 | 10/2019 | Shrivastava et al. | |
| 10,434,605 B2 | 10/2019 | Feth et al. | |
| 11,013,523 B2 | 5/2021 | Jacobi et al. | |
| 11,534,191 B2 | 12/2022 | Ros Fàbrega et al. | |
| 12,161,352 B2 * | 12/2024 | Arad Hadar | A61B 17/22 |
| 2002/0049493 A1 | 4/2002 | Jang | |
| 2003/0009150 A1 | 1/2003 | Pepin | |
| 2003/0023299 A1 | 1/2003 | Amplatz et al. | |
| 2003/0212430 A1 | 11/2003 | Bose et al. | |
| 2003/0212439 A1 | 11/2003 | Schuler et al. | |
| 2004/0024416 A1 | 2/2004 | Yodfat et al. | |
| 2004/0073243 A1 | 4/2004 | Sepetka et al. | |
| 2004/0098099 A1 | 5/2004 | McCullagh et al. | |
| 2004/0143317 A1 | 7/2004 | Stinson et al. | |
| 2004/0167565 A1 | 8/2004 | Beulke et al. | |
| 2004/0199201 A1 | 10/2004 | Kellett et al. | |
| 2004/0199243 A1 | 10/2004 | Yodfat | |
| 2004/0243102 A1 | 12/2004 | Berg et al. | |
| 2004/0260333 A1 | 12/2004 | Dubrul et al. | |
| 2005/0209678 A1 | 9/2005 | Henkes et al. | |
| 2006/0058838 A1 | 3/2006 | Bose et al. | |
| 2006/0064073 A1 | 3/2006 | Schonholz et al. | |
| 2006/0155305 A1 | 7/2006 | Freudenthal et al. | |
| 2006/0293744 A1 | 12/2006 | Peckham et al. | |
| 2007/0118165 A1 | 5/2007 | DeMello et al. | |
| 2007/0188165 A1 | 8/2007 | Kitanaka et al. | |
| 2007/0198028 A1 | 8/2007 | Miloslavski et al. | |
| 2007/0203559 A1 | 8/2007 | Freudenthal et al. | |
| 2007/0208367 A1 | 9/2007 | Fiorella et al. | |
| 2007/0213765 A1 | 9/2007 | Adams et al. | |
| 2007/0276332 A1 | 11/2007 | Bierman | |
| 2007/0288038 A1 | 12/2007 | Bimbo | |
| 2008/0228209 A1 | 9/2008 | DeMello et al. | |
| 2008/0269774 A1 | 10/2008 | Garcia et al. | |
| 2008/0269798 A1 | 10/2008 | Ramzipoor et al. | |
| 2009/0163846 A1 | 6/2009 | Aklog et al. | |
| 2009/0198269 A1 | 8/2009 | Hannes et al. | |
| 2010/0004607 A1 | 1/2010 | Wilson et al. | |
| 2010/0030256 A1 | 2/2010 | Dubrul et al. | |
| 2010/0222864 A1 | 9/2010 | Rivelli et al. | |
| 2011/0160763 A1 | 6/2011 | Ferrera et al. | |
| 2011/0213297 A1 | 9/2011 | Aklog et al. | |
| 2011/0213392 A1 * | 9/2011 | Aklog | A61M 1/3621 606/159 |
| 2012/0059309 A1 | 3/2012 | Di Palma et al. | |
| 2012/0065660 A1 | 3/2012 | Ferrera et al. | |
| 2012/0083868 A1 | 4/2012 | Shrivastava et al. | |
| 2012/0114017 A1 | 5/2012 | Bang et al. | |
| 2012/0116440 A1 | 5/2012 | Leynov et al. | |
| 2012/0179181 A1 | 7/2012 | Straub et al. | |

(56)　　　　References Cited

U.S. PATENT DOCUMENTS

| | | |
|---|---|---|
| 2012/0209311 A1 | 8/2012 | Grandfield et al. |
| 2012/0245671 A1 | 9/2012 | Wainwright et al. |
| 2013/0261638 A1 | 10/2013 | Diamant et al. |
| 2013/0325055 A1 | 12/2013 | Eckhouse et al. |
| 2013/0325056 A1 | 12/2013 | Eckhouse et al. |
| 2014/0052161 A1 | 2/2014 | Cully et al. |
| 2014/0074144 A1 | 3/2014 | Shrivastava et al. |
| 2014/0155908 A1 | 6/2014 | Rosenbluth et al. |
| 2014/0243885 A1 | 8/2014 | Eckhouse et al. |
| 2014/0277015 A1 | 9/2014 | Stinis |
| 2014/0371779 A1 | 12/2014 | Vale et al. |
| 2015/0112376 A1 | 4/2015 | Molaei et al. |
| 2015/0157346 A1 | 6/2015 | Ferrera et al. |
| 2015/0164666 A1 | 6/2015 | Johnson et al. |
| 2015/0231360 A1 | 8/2015 | Watanabe et al. |
| 2015/0359547 A1 | 12/2015 | Vale et al. |
| 2016/0081704 A1 | 3/2016 | Jeon et al. |
| 2016/0256255 A9 | 9/2016 | Ma |
| 2017/0065299 A1 | 3/2017 | Gillespie et al. |
| 2017/0071614 A1 | 3/2017 | Vale et al. |
| 2017/0079767 A1 | 3/2017 | Leon-Yip |
| 2017/0105743 A1 | 4/2017 | Vale et al. |
| 2017/0119408 A1 | 5/2017 | Ma |
| 2017/0119409 A1 | 5/2017 | Ma |
| 2017/0215900 A1 | 8/2017 | Lowinger et al. |
| 2017/0215902 A1 | 8/2017 | Leynov et al. |
| 2017/0239444 A1 | 8/2017 | Parker |
| 2017/0333060 A1 | 11/2017 | Panian |
| 2018/0028209 A1 | 2/2018 | Sudin et al. |
| 2018/0064454 A1 | 3/2018 | Losordo et al. |
| 2018/0126132 A1 | 5/2018 | Heilman et al. |
| 2018/0132876 A1 | 5/2018 | Zaidat |
| 2018/0206862 A1 | 7/2018 | Long |
| 2018/0318062 A1 | 11/2018 | Sudin et al. |
| 2018/0353196 A1 | 12/2018 | Epstein et al. |
| 2018/0361114 A1 | 12/2018 | Chou et al. |
| 2019/0110805 A1 | 4/2019 | Ulm, III |
| 2019/0167284 A1 | 6/2019 | Friedman et al. |
| 2019/0167287 A1 | 6/2019 | Vale et al. |
| 2019/0216476 A1 | 7/2019 | Barry et al. |
| 2019/0239907 A1 | 8/2019 | Brady et al. |
| 2019/0269425 A1 | 9/2019 | Sudin et al. |
| 2019/0269491 A1 | 9/2019 | Jalgaonkar et al. |
| 2019/0274810 A1 | 9/2019 | Phouasalit et al. |
| 2019/0298396 A1 | 10/2019 | Gamba et al. |
| 2019/0307471 A1 | 10/2019 | Friedman et al. |
| 2019/0336727 A1 | 11/2019 | Yang et al. |
| 2020/0000613 A1 | 1/2020 | Shrivastava et al. |
| 2020/0008822 A1 | 1/2020 | Eckhouse et al. |
| 2020/0085444 A1 | 3/2020 | Vale et al. |
| 2020/0205838 A1 | 7/2020 | Walzman |
| 2020/0281612 A1 | 9/2020 | Kelly et al. |
| 2021/0000582 A1 | 1/2021 | Chomas et al. |
| 2021/0059695 A1 | 3/2021 | Haran et al. |
| 2021/0068852 A1 | 3/2021 | Spence |
| 2021/0077134 A1 | 3/2021 | Vale et al. |
| 2021/0177442 A1 | 6/2021 | Girdhar et al. |
| 2021/0236150 A1 | 8/2021 | Arad Hadar |
| 2021/0298775 A1 | 9/2021 | Nguyen et al. |
| 2021/0379350 A1 | 12/2021 | Skillrud et al. |
| 2021/0393279 A1 | 12/2021 | O'Malley et al. |
| 2021/0393280 A1 | 12/2021 | Villazon et al. |
| 2022/0000500 A1 | 1/2022 | Arad Hadar et al. |
| 2022/0117614 A1 | 4/2022 | Salmon et al. |
| 2022/0211400 A1 | 7/2022 | Cox et al. |
| 2022/0265962 A1 | 8/2022 | Garriga et al. |
| 2022/0287765 A1 | 9/2022 | Nageswaran et al. |
| 2022/0354517 A1 | 11/2022 | Behan |
| 2022/0387051 A1 | 12/2022 | Girdhar et al. |
| 2022/0387098 A1 | 12/2022 | Girdhar et al. |
| 2023/0014731 A1 | 1/2023 | Casey et al. |
| 2023/0064470 A1 | 3/2023 | Girdhar et al. |
| 2023/0149021 A1 | 5/2023 | Wainwright |
| 2023/0210544 A1 | 7/2023 | Gamba et al. |
| 2025/0032134 A1 | 1/2025 | Salmon et al. |
| 2025/0160865 A1 | 5/2025 | Arad Hadar |

FOREIGN PATENT DOCUMENTS

| | | |
|---|---|---|
| CN | 104159525 A | 11/2014 |
| CN | 107198554 B | 2/2020 |
| EP | 1427087 A1 | 6/2004 |
| EP | 2662109 A1 | 11/2013 |
| EP | 3266391 A1 | 1/2018 |
| ES | 2341978 T3 | 6/2010 |
| ES | 2381099 T3 | 5/2012 |
| GB | 2498349 A | 7/2013 |
| JP | 2005500138 A | 1/2005 |
| WO | WO99/45835 A2 | 9/1999 |
| WO | WO02/087677 A2 | 11/2002 |
| WO | WO03/075793 A1 | 9/2003 |
| WO | WO2004/002564 A1 | 1/2004 |
| WO | WO2005/027751 A1 | 3/2005 |
| WO | WO2008/124567 A1 | 10/2008 |
| WO | WO2008/157202 A1 | 12/2008 |
| WO | WO2009/014723 A1 | 1/2009 |
| WO | WO2009/105710 A1 | 8/2009 |
| WO | WO2011/068924 A1 | 6/2011 |
| WO | WO2011/082319 A1 | 7/2011 |
| WO | WO2012/106657 A2 | 8/2012 |
| WO | WO2012/156924 A1 | 11/2012 |
| WO | WO2012/158269 A1 | 11/2012 |
| WO | WO2013/008233 A1 | 1/2013 |
| WO | WO2013/152327 A1 | 10/2013 |
| WO | WO2014/008460 A2 | 1/2014 |
| WO | WO2014/127389 A2 | 8/2014 |
| WO | WO2014/204860 A1 | 12/2014 |
| WO | WO2015/006782 A1 | 1/2015 |
| WO | WO2015/189354 A1 | 12/2015 |
| WO | WO2016/113047 A1 | 7/2016 |
| WO | WO2017/072663 A1 | 5/2017 |
| WO | WO2017/074290 A1 | 5/2017 |
| WO | WO2017/075544 A1 | 5/2017 |
| WO | WO2018/080590 A1 | 5/2018 |
| WO | WO2018/160966 A1 | 9/2018 |
| WO | WO2019/055311 A1 | 3/2019 |
| WO | WO2019/064306 A1 | 4/2019 |
| WO | WO2019/178131 A1 | 9/2019 |
| WO | WO2020/021333 A2 | 1/2020 |
| WO | WO2020/079082 A1 | 4/2020 |
| WO | WO2020/099386 A1 | 5/2020 |
| WO | WO2021/016213 A1 | 1/2021 |
| WO | WO2023/117919 A1 | 6/2023 |

OTHER PUBLICATIONS

Villazón et al., U.S. Appl. No. 18/641,098 entitled "Device and a thrombectomy apparatus for extraction of thrombus from a blood vessel", filed Apr. 19, 2024.

Garcia Sabido et al.; U.S. Appl. No. 18/722,456 entitled "An intravascular device with an improved attachment of its elements and a method of manufacturing thereof," filed Jun. 20, 2024.

Garcia Sabido et al.; U.S. Appl. No. 18/722,470 entitled "An intravascular device with an improved attachment of its elements and a method of manufacturing thereof," filed Jun. 20, 2024.

Salmon et al; U.S. Appl. No. 18/447,854 entitled "Thrombectomy system and method of use," filed Aug. 10, 2023.

Garcia Sabido et al; U.S. Appl. No. 18/546,190 entitled "An expandable clot mobilizer device for extraction of an occlusion from a blood vessel," filed Aug. 11, 2023.

Garcia Sabido et al.; U.S. Appl. No. 18/546,206 entitled "A self expandable medical device for advancement through vasculature to an expansion site in a blood vessel," filed Aug. 11, 2023.

Arad et al.; U.S. Appl. No. 62/760,786 entitled "Thrombectomy system comprising an expandable tip aspiration catheter and clot-capture element," filed Nov. 13, 2018.

Berkhemer et al.; A randomized trial of intraarterial treatment for acute ischemic stroke; New England Journal of Medicine; 372; pp. 11-20; Jan. 1, 2015.

(56) References Cited

OTHER PUBLICATIONS

Bouthillier et al.; Segments of the internal carotid artery: a new classification; Neurosurgery; 38(3); pp. 425-433; Mar. 1, 1996.

Ceretrieve; 3 pages; retrieved from the internet (http://trendlines.com/portfolio/ceretrieve/) on Sep. 13, 2018.

Duffy et al.; Novel methodology to replicate clot analogs with diverse composition in acute ischemic stroke; Journal of neurointerventional surgery; 9(5); pp. 486-491; May 1, 2017.

Fennell et al.; What to do about fibrin rich "tough clots"? Comparing the Solitaire stent retriever with a novel geometric clot extractor in an in vitro stroke model; Journal of neurointerventional surgery; 10(9); pp. 907-910; Sep. 1, 2018.

Mokin et al.; Stent retriever thrombectomy with the Cover accessory device versus proximal protection with a balloon guide catheter: in vitro stroke model comparison; Journal of neurointerventional surgery; 8(4); pp. 413-417; Apr. 1, 2016.

Castano et al.; Unwanted detachment of the Solitaire device during mechanical thrombectomy in acute ischemic stroke; Journal of neurointerventional surgery; 8(12); pp. 1226-1230; Dec. 1, 2016.

Penumbra Inc.; Recalls 3D revascularization device due to wire material that may break or separate during use; FDA Recall; retrieved from the internet (http://web.archive.org/web/20200813123505/https:/www.fda.gov/medical-devices/medical-device-recalls/penumbra-inc-recalls-3d-revascularization-device-due-wire-material-may-break-or-separate-during-use).

Garcia-Sabido et al.; U.S. Appl. No. 18/040,492 entitled "A clot mobilizer device for extraction of an occlusion from a blood vessel," filed Feb. 3, 2023.

Garcia-Sabido et al.; U.S. Appl. No. 18/040,495 entitled "An elongated device with an improved attachment of its elements," filed Feb. 3, 2023.

Ríos Garriga et al; U.S. Appl. No. 19/094,121 entitled "Delivery catheter device and system for accessing the intracranial vasculature," filed Mar. 28, 2025.

* cited by examiner

310

305     300

305

300

305

300

THROMBECTOMY DEVICE, SYSTEM AND METHOD FOR EXTRACTION OF VASCULAR THROMBI FROM A BLOOD VESSEL

CROSS REFERENCE TO RELATED APPLICATIONS

This application is a continuation-in-part of U.S. application Ser. No. 17/235,764, filed on Apr. 20, 2021, which is a continuation of U.S. application Ser. No. 15/649,266, filed Jul. 13, 2017, now U.S. Pat. No. 11,013,523, which is a continuation-in-part of PCT/EP2015/079400, filed Dec. 11, 2015, which claims priority to Spanish application No. P201530028, filed Jan. 13, 2015; a continuation-in-part of U.S. application Ser. No. 17/274,973, filed Oct. 16, 2019, as PCT/EP2019/078088, which claims priority to European Patent Application No. 18382736.9, filed Oct. 16, 2018; a continuation-in-part of U.S. application Ser. No. 17/291, 696, filed Nov. 12, 2019, as PCT/EP2019/080993, which claims priority to European Application No. 18382800.3, filed Nov. 13, 2018; and is a continuation-in-part of U.S. application Ser. No. 17/500,844 filed on Oct. 12, 2021, which claims the benefit of U.S. Provisional Patent Application No. 63/093,540, filed Oct. 19, 2020, each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE DISCLOSURE

The present invention relates to a thrombectomy device, system and methods for extraction of vascular thrombi from a blood vessel.

Endovascular treatment has been employed in cases of stroke since the 1990s. The number of patients it has been used on has grown slowly but steadily. The main obstacle for wide use of these highly complex treatments is the need for a more coordinated medical system, at various levels. The main goal of these medical networks is to ensure that patients can get to centers with required capabilities within 6-8 hours of symptom onset.

The first positive randomized study was published (Berkhemer O. A. et al. "A randomized trial of intraarterial treatment for acute ischemic stroke." N Engl J Med. January 2015; 372: 1 1-20. doi: 10.1056/NEJMoa141 1587. Epub 17 Dec. 2014. PubMed PMID: 25517348) demonstrating the efficacy of the thrombectomy treatment as compared to more conventional medical treatments by reducing the disability rate three months after a stroke. In addition, four other major similar clinical trials were published in 2015 definitively confirming the superiority of thrombectomy treatment with latest-generation devices by reducing impairment as compared to other medical treatments.

With regard to endovascular treatment, initially the strategy was local perfusion of a fibrinolytic agent through a microcatheter directly into the thrombus. In the early 2000s, a new device was introduced that appeared to be more effective than intraarterial fibrinolysis. It was a spiral that opened around the thrombus, facilitating its extraction (MERCi®)). In 2006, a system basically based on bringing a large-gauge catheter in close proximity to the thrombus in order to aspirate it became popular. The catheter is connected to a continuous aspiration pump (Penumbra®). This system has evolved over the years, seeking to attain a catheter with an increasingly large diameter, able to navigate close to the thrombus.

The use of the so-called stent retrievers began around 2009. Their use consists of crossing the thrombus with a microcatheter, then advancing the stent through the microcatheter. Once the distal end of the sheathed device has reached the most distal part of the thrombus, the stent is unsheathed, self-expanding at the thrombus level and captures the thrombus. It is advisable to wait several minutes with the stent expanded to increase the engagement of the thrombus and then withdraw the expanded stent with the intention of it dragging the thrombus. This final step can be done while aspirating through the catheter to try to reverse the flow and thus increase the chances of recovering the thrombus. Stent retrievers have entirely displaced the first-generation devices described above due to their high efficacy, ease to use and reduced procedure times.

In addition, when using a stent retriever, a guide balloon catheter is often used. This catheter only advances to locations distant from thrombi sites. Upon inflation of the balloon situated at the end of the catheter, the catheter is able to stop the flow in the arterial segment distal to the balloon, which is where the thrombus to be extracted is located. By aspirating through it, the flow in the arterial segment distal to the balloon can be reversed in order to facilitate the removal of the thrombus together with the stent retriever.

There are two categories of thrombectomy devices, mechanical thrombectomy devices (e.g., stent retrievers) and aspiration devices, both with limitations and complications.

An example of a thrombectomy device is described in WO2011/082319, with a variety of interchangeable tips according to the needs of the surgeon during thrombectomy procedure. In all cases, the device described in this document has to cross the interior of the thrombus or pass between the thrombus and the arterial wall before being expanded. Furthermore, in all cases the thrombus must be fragmented to be dissolved by natural or artificial means. As result of these operational principles, this device does not allow the removal of the thrombus in a way that ensures there will be no distal embolization due to a release of clot fragments.

Another example, WO 02/087677 A2 discloses an apparatus and methods used to prevent the introduction of emboli into the bloodstream during and after surgery performed to reduce or remove blockage in blood vessels. Unlike the present invention, the reference device does not have a distal end configured to reduce or stop the flow of the artery, much less reverse it.

Additionally, stent-retrievers of the present art will, upon deployment, need time (up to three minutes) to acclimatize to the thrombus prior to retrieving the thrombus to minimize fracturing of the thrombus. When dealing with a potential stroke, time is of the essence, and the current device can be used to retrieve the thrombus immediately upon arrival by aspiration.

Therefore, it would be beneficial to provide a thrombectomy device increasing procedural success, preventing fragmentation and distal migration, regulating blood flow during a thrombectomy, etc. It is also beneficial to provide an automated thrombectomy device and system that may be used in both traditional (hospital) and non-traditional (nursing home, assisted care facility) environments with greater deployment and usage to expedite the removal of the thrombus, significantly improving patient outcomes, and restoring blood flow. At least some of these objectives will be met by the various embodiments that follow.

SUMMARY OF THE DISCLOSURE

The device and system of the present invention manages to resolve the aforesaid disadvantages, providing other advantages that will be described below.

One aspect of the invention provides a thrombectomy device having a delivery catheter; and an expandable occlusion member configured to be movably disposed within the delivery catheter in a retracted position and at least partially outside the delivery catheter in an extended position, the occlusion member comprising a non-permeable coating or covering, a diameter of a distal end of the occlusion member being greater in the extended position than in the retracted position, the occlusion member in its extended position being configured to adapt its shape and length to a surrounding blood vessel such that the occlusion member expands to a diameter of the blood vessel and occludes the blood vessel and such that the occlusion member lengthens as it narrows to retain a thrombus within the occlusion member during movement of the occlusion member through the blood vessel.

In some examples, a thrombectomy device may have a tapered dilator catheter configured to be movably disposed within the delivery catheter, wherein the occlusion member is configured to remain within the delivery catheter after the dilator catheter has been removed. In some examples, the delivery catheter, dilator catheter and occlusion member can be oriented on the same axis.

In some examples, the occlusion member can be self-expandable. The occlusion member comprises a shape memory material. The shape memory material may comprise nitinol. The occlusion member can have a diameter at its distal end of between 2 millimeters and 20 millimeters. Depending on the diameter of the vessel, the occlusion member can have a diameter at its distal end between 5 and 15 millimeters. For example, the occlusion member can have a diameter at its distal end near 5 millimeters or near 6 millimeters.

In some examples, the occlusion member comprises a thrombus retaining element. The thrombus retaining element may comprise a sharp physical element. The delivery catheter and occlusion member can be oriented on the same axis. The expandable occlusion member may comprise an expandable funnel.

In some examples, the thrombectomy device may have a resheathing element adapted to reintroduce the occlusion member into the delivery catheter. The resheathing element may comprise a cannula, a clamp, a funnel, or any combination of them.

In some examples, the thrombectomy device may have an aspiration catheter comprising the occlusion member and a tube extending proximally from a proximal opening of the occlusion member, the aspiration catheter being configured to aspirate and capture the thrombus within the occlusion member. The occlusion member may have a proximal end with a diameter equal to a diameter of a distal end of the tube, providing a smooth connection.

In some examples, the delivery catheter is configured to deliver the occlusion member to a peripheral artery. The peripheral artery may be a renal artery. The peripheral artery may be a mesenteric artery. The peripheral artery may be a femoral artery. The peripheral artery may be a popliteal artery. The peripheral artery may be a tibial artery. The peripheral artery may be a vertebral vessel. The peripheral artery may be a perineal artery. The peripheral artery may be a hepatic artery. The peripheral artery may be a splenic artery. The peripheral artery may be an iliac artery.

In some examples, the delivery catheter is configured to deliver the occlusion member to a vascular artery. The vascular artery may be a coronary artery. The vascular artery may be a pulmonary artery.

In some other examples, the delivery catheter is configured to deliver the occlusion member to a vein. The vein may be a vein located in the peripheral vascular system. The vein may be located in the central vascular system.

One aspect of the invention provides a system for extraction of vascular thrombi from a blood vessel comprising the thrombectomy device as described herein, wherein the system further comprises a communications channel, a control module, a data storage device, and a guidance system, wherein the control module is guided by a computer-assisted controller.

In some examples, the system may have an imaging device, a first radiomarker, and a second radiomarker, wherein the first radiomarker is arranged and configured to indicate a location of the distal end of the occlusion member, and the second radiomarker is arranged and configured to indicate a location of the thrombus. In other examples, the system may have an imaging device, wherein the thrombectomy device further comprises a radiopaque marker. The radiopaque marker is arranged and configured to indicate a location of the occlusion member.

One aspect of the invention provides a method of extracting a thrombus from a thrombus site in a blood vessel of a patient, the method comprising: advancing a delivery catheter and an expandable occlusion member through vasculature of the patient toward the thrombus site with the occlusion member disposed in a retracted position proximal to the distal end of the delivery catheter; moving the occlusion member and delivery catheter with respect to each other to place the occlusion member in an extended position at least partially outside of the delivery catheter; occluding the blood vessel with the occlusion member; moving the thrombus at least partially into the occlusion member; moving the occlusion member and the thrombus proximally within the vasculature; and adapting a shape and length of the occlusion member to a surrounding blood vessel of the vasculature such that the occlusion member lengthens as it narrows to retain the thrombus within the occlusion member as it moves within the blood vessel.

In some examples, the occluding step comprises expanding a distal end of the occlusion member to a diameter of the blood vessel proximal to the thrombus site. The moving step may comprise expanding a distal end of the occlusion member. The expanding step may comprise allowing the occlusion member to self-expand. The expanding step may comprise decreasing a length of the occlusion member.

In some examples, the advancing step may comprise advancing the delivery catheter and the occlusion member along a common axis. The method may include a step of moving the occlusion member proximally into the delivery catheter after moving the thrombus into the occlusion member.

In some examples, the method may include a step of advancing a tapered dilator catheter with the delivery catheter and the occlusion member through vasculature of the patient toward the thrombus site with a distal end of the tapered dilator catheter disposed distal to a distal end of the delivery catheter. The method may include a step of retracting the dilator catheter into the delivery catheter. The retracting step may be prior to moving the occlusion member and delivery catheter with respect to each other to place the occlusion member in an extended position at least partially outside of the delivery catheter.

In some examples, the advancing step may comprise advancing the delivery catheter, the tapered dilator catheter and the occlusion member along a common axis. The thrombus site may be in a vascular artery. The vascular artery may be a coronary artery, a pulmonary artery, or a peripheral artery. The peripheral artery may be a renal artery, a mesenteric artery, a femoral artery, a popliteal artery, a tibial artery, a vertebral vessel, a perineal artery, an iliac artery, a hepatic artery, or a splenic artery. The thrombus site may be in a vein. The vein may be in the peripheral vascular system. The vein may be in the central vascular system. The step of moving the thrombus may comprise aspirating the thrombus into the occlusion member.

In some examples, the occlusion member is disposed at a distal end of an aspiration catheter, and the aspirating step may comprise applying vacuum to the occlusion member through the aspiration catheter.

In some examples, the occlusion member may be used in combination with other auxiliary coaxial devices. The auxiliary device may be retrieval device such as a clot mobilizer (e.g., stent retriever or ClotTriever™ Thrombectomy System). The auxiliary device may be a distal access catheter (e.g., distal aspiration catheter). The auxiliary device may be an atherectomy device (e.g., Rotablator™ rotational atherectomy device). The auxiliary device may be a distal protection device. The auxiliary device may be a rheolytic device.

BRIEF DESCRIPTION OF THE DRAWINGS

For a better understanding of the foregoing, several drawings are attached, which schematically and solely by way of non-limiting example represent a practical case of the embodiment.

DETAILED DESCRIPTION

Figure 1A:
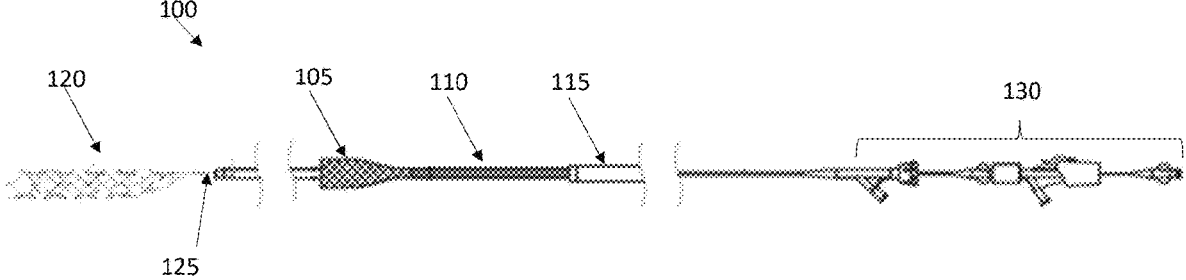
FIG. 1A is a schematic elevational view of the thrombectomy device according to the present invention in its approaching configuration, which is used for clearing the way through blood vessels and reaching the vessel where the thrombus is located.

A thrombectomy device according to the present invention can be particularly suited to remove a thrombus from a vessel in an atraumatic manner while preventing distal migration. As described herein, the thrombectomy device may comprise an advancement tool (e.g., a catheter) having an occlusion member locatable at a distal end, a delivery catheter in which the advancement tool and occlusion member are disposed, and an optional auxiliary coaxial device (e.g., a clot-capture element). The delivery catheter can be configured to facilitate a transition of the occlusion member between a compressed state and an expanded state (e.g., deployed state) as the occlusion member emerges from a distal end of the delivery catheter.

The delivery catheter may be configured to navigate to the site of a thrombus in a target vessel during use in a thrombectomy procedure. The advancement tool and occlusion member may be disposed within the delivery catheter (acting as a carrier) to deliver the occlusion member (e.g., expandable funnel) to an operative position at or near a thrombus within the target vessel. For example, the advancement tool may be extendable through the delivery catheter lumen. In some examples, the delivery catheter may have a deflectable distal end configured to navigate tortuous vasculature while navigating the thrombectomy device to the thrombus within the target vessel. In some examples, the delivery catheter may have a continuous body along a length from a proximal end to a distal end. The delivery catheter body may have different regions or areas of flexibility or rigidity to facilitate advancement during navigation through a vessel. For example, a distal end of the delivery catheter may be sufficiently flexible and deflectable to accommodate vessel tortuosity and a proximal portion or region may be less flexible compared to the distal end to facilitate increased column strength of the delivery catheter and direct a force for advancing the delivery catheter within (e.g., through) the vessel. In some examples, the delivery catheter body may be connected to a proximal pusher (e.g., pusher wire) to facilitate the advancement of the delivery catheter through the vasculature (e.g., through a coronary artery or a pulmonary artery). In some other examples, the delivery catheter may be an introducer sheath (e.g., when navigating in a vessel with a target site close to the insertion or puncture point). For example, the insertion point may be in the groin for treating vessels located in the lower limbs, vessels located in the central vascular system or vessels located in the neurovasculature. The insertion point may be near the arm chelidon for vessels located in the upper limbs. The insertion point may be in the jugular vein.

The thrombectomy device of this invention may be used to remove thrombi from veins or vascular arteries. The delivery catheter, advancement tool, occlusion device, and optional auxiliary coaxial device may be adapted to aspects of the blood vessel and thrombus site, such as blood vessel diameter, distance from the insertion point to the thrombus site, and nature of the thrombus.

FIG. 1A illustrates an example of a thrombectomy device 100 according to the present invention. Therein it is illustrated a scheme of an expanded configuration of the thrombectomy system, which in this embodiment includes an occlusion member 105 (which may optionally be shaped like a funnel) at a distal end of an advancement tool, such as a catheter 110. The distal end of the thrombectomy device 100 can be configured to be inserted (e.g., introduced) into vasculature of a patient and advanced to a thrombus site within a blood vessel. Thrombectomy device 100 also includes a guide catheter 115 (e.g., a delivery catheter); an optional clot-capture element 120, such as a stent retriever, and an optional microcatheter 125 for advancing the clot-capture element.

In some examples, the proximal end of the thrombectomy device 100 may be operably coupled to one or more controls, hubs, or additional elements that can be configured to operate one or more components of the thrombectomy device. For example, FIG. 1A shows a hub 130 having one or more connections that may facilitate one or more of navigation, deployment, aspiration, expansion, compression, advancement, retraction of the thrombectomy device, etc., when in use.

Figure 1B:
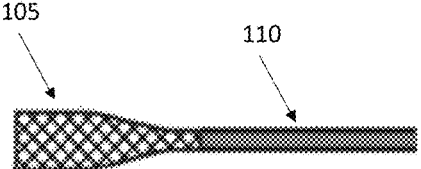
FIG. 1B is a schematic elevational view of the thrombectomy device according to the present invention in its retracted or navigational configuration.

FIG. 1B shows a detailed view of the distal end of the thrombectomy device 100 including the occlusion member 105 coupled to the advancement tool 110. In some examples, the occlusion member is deployable from within the delivery catheter as the advancement tool 110 is advanced distally from therein or as the delivery catheter is withdrawn from the advancement tool 110 and occlusion member 105. Occlusion member 105 is illustrated as a funnel in FIGS. 1A and 1B and, in some embodiments, comprises an arrangement of filaments (e.g., a mesh). In some examples, the occlusion member 105 may be coupled, or configured to couple, to a distal end of the advancement tool 110. In some examples, the occlusion member may be region or segment of the distal end of the advancement tool. Details of one embodiment of the occlusion member are discussed below with respect to FIGS. 2A-B.

A thrombectomy device according to the present invention may comprise a plurality of catheters in operable communication with one another. For example, the thrombectomy device may comprise a tapered dilator catheter, an aspiration catheter, a delivery catheter, a sheathing catheter, an introducer catheter or sheath, or any combination thereof. In some examples each catheter comprising the device may be configured to be coaxially aligned with one another. For example, a dilator catheter may comprise a tapered distal tip and extend through a lumen of the thrombectomy device and can be configured to dilate a vessel to facilitate navigation of the thrombectomy device through the vasculature.

In some examples, the advancement tool may comprise an elongate member that extends from a proximal end to a distal end. The distal end of the advancement tool may comprise the occlusion member (e.g., expandable funnel) as a distal region of the advancement tool. For example, the expandable funnel may be an expandable region of the advancement tool distal end. In some examples, the occlusion member (e.g., expandable funnel) is operably coupled (e.g., affixed) to the distal end of the advancement tool.

The occlusion member may transition from a compressed state during delivery to an expanded state in use at the thrombectomy target site. In a compressed state, a diameter of the occlusion member may be generally uniform from a proximal end to a distal end (e.g., a distal perimeter of the expandable funnel). The diameter of the occlusion member may increase along one or more annular regions as the funnel transitions from the compressed state to the expanded state. In some examples, transition of the expandable occlusion member from the compressed state to the expanded state can occur when the occlusion member is advanced distally from a delivery catheter or sheath or when the delivery catheter or sheath is withdrawn proximally from the occlusion member.

In some examples, the occlusion member can be configured to expand at or near a thrombus site so that at least part of the occlusion member is in apposition to an interior wall of a blood vessel (e.g., a peripheral artery/vein or a central vascular system vessel) near the thrombus to reduce or stop the flow of blood at the thrombus site. The occlusion member may be formed from a shape memory material that is configured to expand with an outwardly directed radial force toward a preset shape. The outward radial force exerted by portions of the occlusion member not in contact with the blood vessel wall help maintain the occlusion member in its open configuration against the force exerted by the surrounding blood. The occlusion member may be configured to exert sufficient outward force in blood vessels with diameters between about 2 mm and 20 mm (both inclusive), or between about 3 mm and 6 mm, for example near 5 mm or near 6 mm. The outward radial force of the occlusion member may be augmented by the spring force from loops formed in the filaments of the occlusion member mesh at the distal end of the occlusion member. The loops may also provide an atraumatic distal tip. The loops may be formed by bending the filaments at the distal end coming from the proximal end of the occlusion member toward the proximal end of the occlusion member, forming distal closed loops. The occlusion member may be compressed within its delivery catheter against the outward radial force during delivery prior to a thrombectomy procedure or during retraction at the end of a thrombectomy procedure. The occlusion member may be configured with a specific length, diameter and shape to capture, engage and/or retain a thrombus from different blood vessels. The occlusion member may be configured to exert a specific outward radial force to the vessel, due to the specific diameter, length, and/or shape.

In some examples, the occlusion member may be covered or coated with a non-permeable film (or coating) configured to reduce or stop blood flow while the thrombus is captured. Depending on the target site, the occlusion member can reduce or stop blood flow passing or contacting the occlusion member. The coating may be non-permeable (e.g., sufficiently non-permeable) to prevent a fluid to pass through. The coating may be made of one or combination of more than one biocompatible materials. The coating may comprise a polymer such as silicone or polyurethane, among others. In an embodiment, the coating thickness is in the range between 5 and 25 μm, particularly 15 μm. In some examples, the coating may be permeable or have one or more apertures extending from an interior to an exterior of the occlusion member in an expanded state. For example, a plurality of perforations may be arranged on and through the occlusion member (e.g., expandable funnel) configured to allow less than an unrestricted flow of blood to flow therethrough when the occlusion member is in an expanded state. The non-permeable coating is configured to make the device atraumatic and achieve a smooth advancement through vessels. In some examples, the occlusion member 200 spreads the radial force loaded over the arterial wall over its entire length, combination of the expandable funnel and the non-permeable coating between its filaments. The non-permeable coating may be included in different regions (sections) of the occlusion member. In some examples, the entire occlusion member comprises a non-permeable coating. In some examples, less than the entire occlusion member comprises a non-permeable coating. In some examples, one or more sections of the occlusion member comprise a non-permeable coating. For example, a distal tubular section (e.g., 205) may be coated; a distal conical section (e.g., 211) may be coated; a conical section (e.g., 210) may be coated; a proximal tubular section (e.g., 215) may be coated; or a combination thereof.

Figures 2A, 2B:
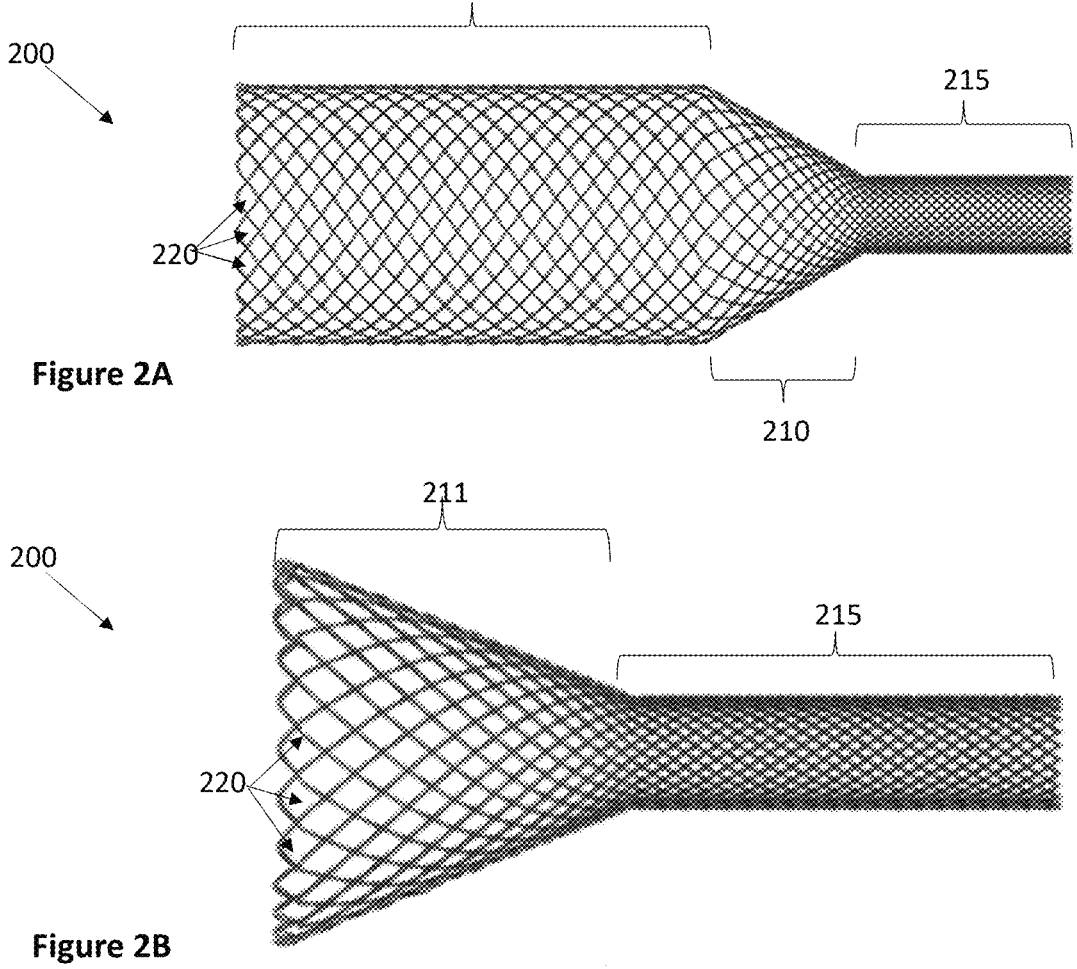
FIG. 2A is a schematic elevational view of an occlusion member of a thrombectomy device according to the present invention.
FIG. 2B is a schematic elevational view of an occlusion member of a thrombectomy device according to the present invention.

The occlusion member can have an expanded shape adapted to the features of the target blood vessel and/or of the thrombus. FIGS. 2A and 2B illustrate two examples of an occlusion member 200. In the embodiment shown in FIG. 2A, the expandable occlusion member 200 is formed as a mesh of at least two sets of intertwined helicoidal filaments of shape memory material (such as, e.g., Nitinol) extending in opposite directions. The operational features of occlusion member 200 depends on, among other factors, the material, the density of the filaments forming the mesh, and the braiding angle of the filaments. The occlusion member 200 is configured to self-expand differently in different regions, such as a distal region (e.g., annular/tubular region) 205, a tapered (or conical) region 210 and a proximal region 215 having a diameter less than distal region 205. The distal region 205 is shown as a length of annular/tubular mesh configured to expand when deployed from within the delivery catheter (not shown). In some examples, the occlusion member may comprise a number of filaments providing a filament mesh density configured to support and provide the operation characteristics of the occlusion member. In some examples, the occlusion member 200 may comprise a one or more filaments. In some examples, the number of filaments may be between 1 and 100. For example, the number of filaments may be 1, 5, 10, 15, 20, 25, 30, 35, 40, 45, 50, 55, 60, 65, 70, 75, 80, 85, 90, 95, 100, or more, or any number of filaments therebetween. For example, the occlusion member may comprise between 12 and 48 filaments (both inclusive). For examples, the occlusion member may comprise 12 filaments, 18 filaments, 24 filaments or 48 filaments.

In this embodiment, the filaments bend back proximally from the distal end of the occlusion member 200 to form closed loops 220. Because of the nature of the filaments forming them, the closed loops 220 act as springs that provide a radially outward expansion force to distal region 205 to augment the radial force provided by the shape memory material of the occlusion member as the distal region 205 of the occlusion member expands to be in apposition to an interior wall of a blood vessel. In some examples, the closed loops 220 provide an atraumatic tip configured to facilitate navigation of the thrombectomy device with the patient's vasculature.

The tapered region 210 of the embodiment of FIG. 2A extends between the distal region 205 and the proximal region 215. The tapered region 210 can transition from a compressed state to a conical expanded state, as illustrated in FIG. 2A. Especially in embodiments in which the tapered region is covered by a coating, as described above, tapered region 210 has features enabling it to remain expanded against the force applied by the pressure of the blood around it, thereby reducing or even stopping blood flow in the vessel. In some examples, reducing or stopping blood flow (e.g., the extent or level of occlusion may be based on or depending on the target site characteristics and/or procedural requirements. For example, the braiding angle of the filaments at the transition from the proximal region 215 to the tapered region 210 and/or at the transition between the tapered region 210 and the distal region 205 may provide enhanced radial strength to keep distal region 205 open and against the blood vessel wall.

Proximal region 215 may be attached to an advancement tool (not shown), such as a catheter (e.g., an aspiration catheter, such as the catheter 110 shown in FIG. 1A) or a push wire. Also not shown is the compressed state of the occlusion member where the distal region 205, tapered region 210, and proximal region 215 can have the same or similar diameter when retained in a compressed state within the delivery catheter.

In some examples, the length of the distal region may be configured based on an application or use. For example, application of a thrombectomy device according to the present invention may benefit from a distal region 205 having an extended length from the distal end of the tapered region 210 to the plurality of closed loops at the distal end of the distal region.

In the embodiment of FIG. 2B, the occlusion member has a distal region 211 shaped as a funnel shown in an expanded configuration and tapering proximally (e.g., decreasing diameter) to the proximal region 215. In some examples, the plurality of closed loops 220 around a distal perimeter of distal region 211 act as springs to provide an expansion force in addition to the expansion force of the shape memory material forming the occlusion member. In some examples, the closed loops may be coplanar with the funnel. This configuration can be used in target sites in a blood vessel with length restrictions (e.g., having a short deployment or landing site, i.e., the site where the device is deployed), in result, the first region 211 with conical shape may expand to contact the interior wall of the blood vessel. For example, the radial force providing expansion of the conical shaped occlusion member may be configured to adapt a shape, length, or other dimension of the conical shape to the contact, complement, engage, or otherwise adapt to the vessel wall anatomy (e.g., regular or irregular surfaces, cavitations, etc. of the tunica intima).

The occlusion member can be configured to expand outward and contact an interior of a blood vessel. Accordingly, an exterior of the first region 210 may expand to contact the interior wall of the blood vessel and may adapt its shape and length to the wall anatomy. In some examples, the plurality of closed loops 220 at a distal tip of the occlusion member may expand to contact the interior of the blood vessel. In some examples, one or more regions of the occlusion member may be adaptable to the vessel geometry. For example, one or more regions of the occlusion member can be configured to expand as it is deployed and conform to an interior surface and/or the geometric characteristics of the vessel. In some examples, conforming to the vessel may involve the occlusion member being adjusted or adjustable relative to one or more dimensions to accommodate navigation and use within a blood vessel. For example, in a deployed state, the length of the occlusion member (e.g., one or more regions) may increase as a diameter decreases. In some examples, the increase in length may be proportional to the decrease in diameter. In another example, the length of the occlusion member may decrease as a diameter of the occlusion member increases. In some examples, the changes in the length may be inversely related to changes in a diameter of the occlusion member. In some examples, changes in the length may be directly related to a change in the diameter of the occlusion member.

In some examples, an interior of the occlusion member can be configured to accommodate thrombus material therein. For example, a clot-capture element may be advanced from a central lumen of the thrombectomy device to contact and capture a thrombus then be retracted proximally back towards and at least partially into the occlusion member. Alternatively, or additionally, aspiration can be applied to the interior of the occlusion member (via, e.g., an aspiration catheter attached to, and communicating with, the distal region of the occlusion member) to pull thrombus material into the occlusion member.

The occlusion member may be configured to modulate a flow of blood through the vessel. As the occlusion member is deployed into an expanded state, a flow of blood within the vessel may be partially reduced or completely stopped. Expansion of the occlusion member can be sufficient to maintain an expanded state against pressure from the flow of blood thereby reducing or stopping a flow of blood past the occlusion member during a thrombectomy procedure. In some examples, decreasing the flow of blood within the vessel can promote successfully capture and extraction of the thrombus by a thrombectomy device described herein.

Figures 3A, 3B, 3C:
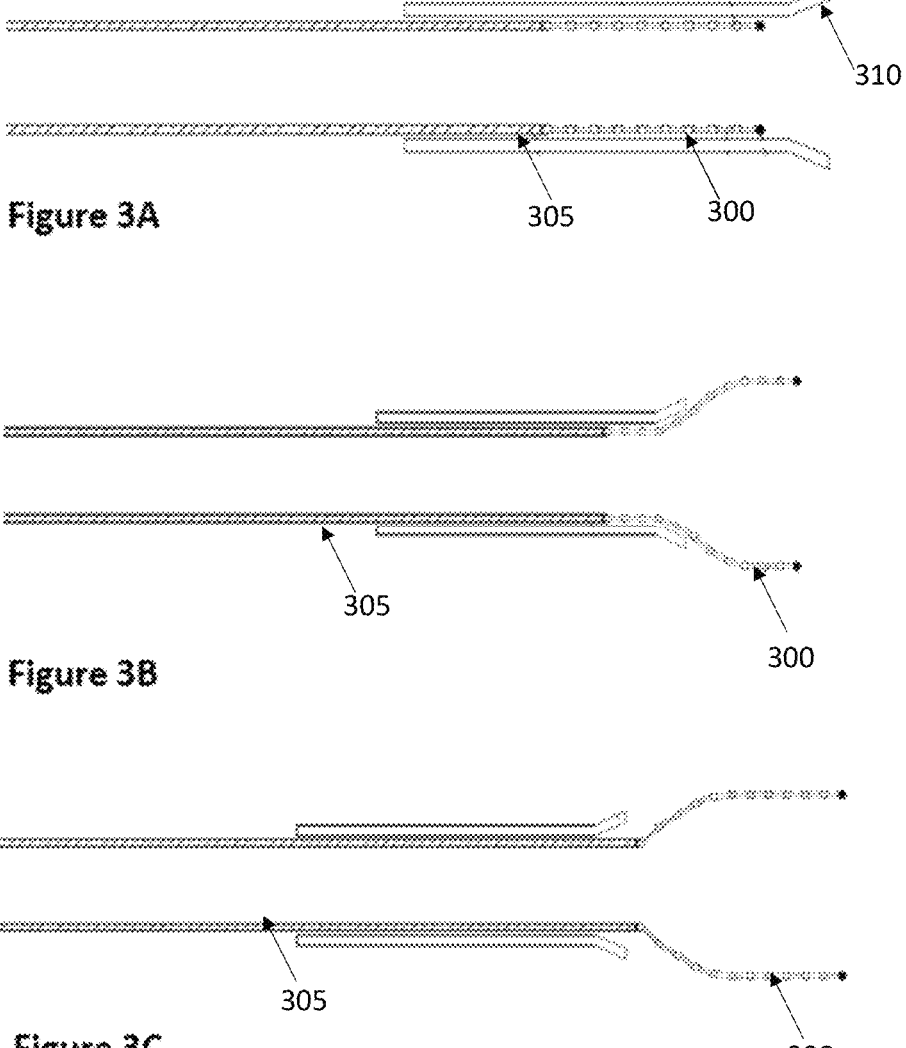
FIGS. 3A to 3C are schematic elevational views showing cross-sections of a thrombectomy device and transition of an occlusion member from a compressed state to an expanded state.

The occlusion member may be selectively deployed or transitioned from a compressed state to an expanded state as the occlusion member is advanced from a catheter (e.g., a delivery catheter). Referencing FIGS. 3A to 3C an occlusion member 300 can be delivered through a blood vessel in a compressed state. FIG. 3A shows the occlusion member 300 compressed within a delivery catheter 310 at the distal end of an advancement tool (e.g., catheter) 305 coaxially arranged with the delivery catheter 310. In FIG. 3B, the advancement tool 305 has been advanced (or the delivery catheter 310 withdrawn) to permit the occlusion member 300 to partially expand. FIG. 3C illustrates the occlusion member fully expanded. The occlusion member may be retracted and re-sheathed within delivery catheter 310. Shown in FIGS. 3A to 3C, delivery catheter 310 can be used to facilitate a transition from an expanded state to a compressed state (or in the other way around). In some examples, the occlusion member may be sheathed or transitioned from an expanded state to a compressed state as the funnel catheter 305 is retracted into any elongate member (e.g., catheter). For example, during a thrombectomy, the occlusion member may be compressed by supplying force against its shape memory properties.

Figure 4:
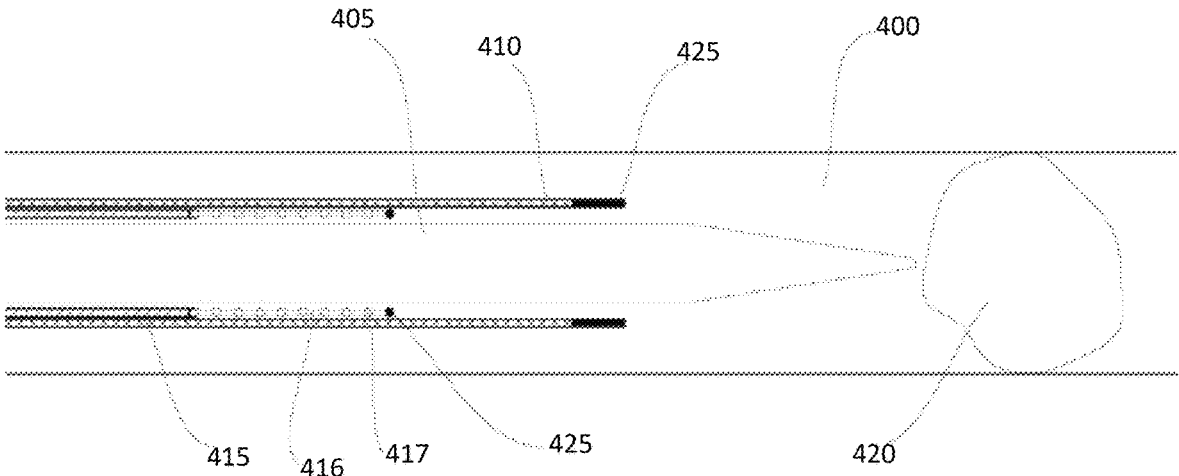
FIG. 4 is a schematic elevational view of a thrombectomy device according to the present invention showing an example of a configuration of the device within a blood vessel.
Figure 5:
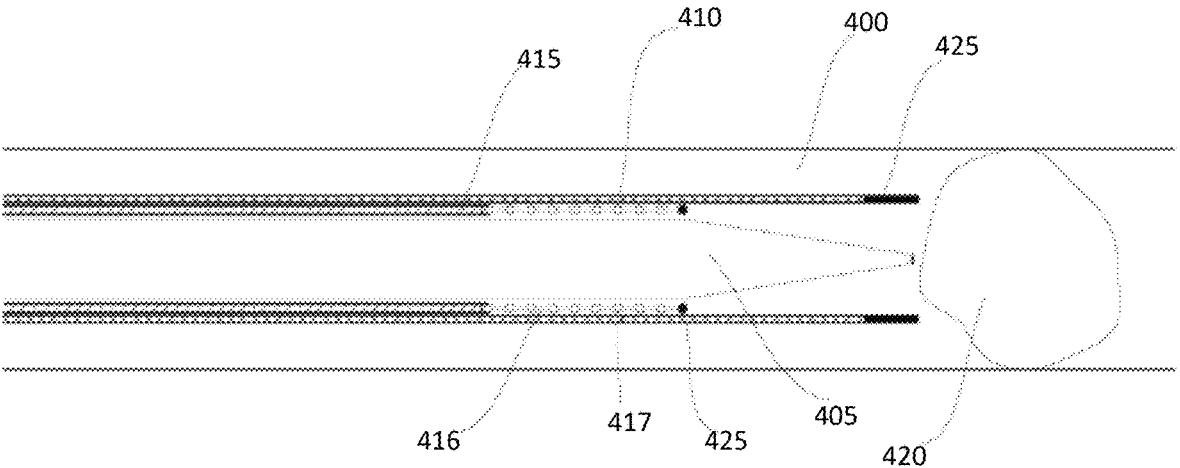
FIG. 5 is a schematic elevational view of a thrombectomy device according to the present invention showing an example of a configuration of the device proximal to an occlusion site within a blood vessel.
Figure 6:
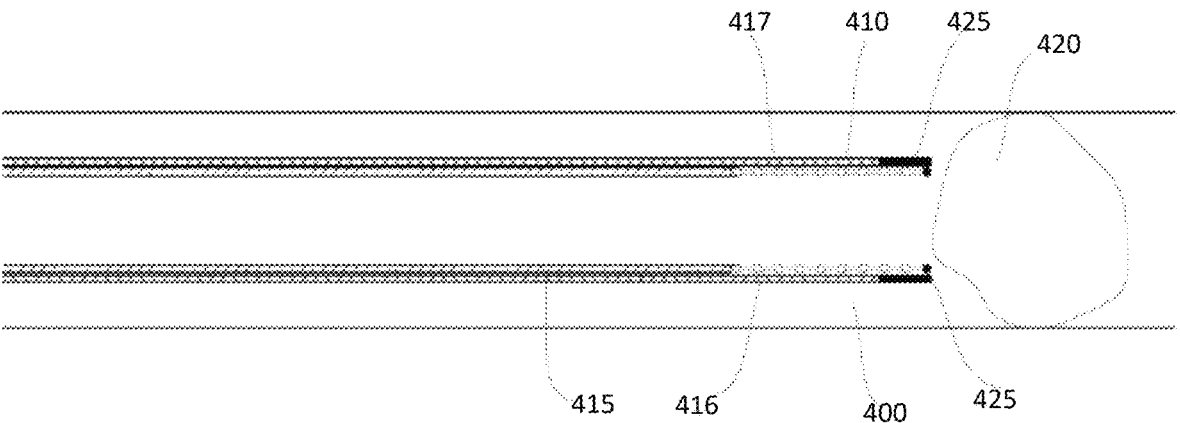
FIG. 6 is a schematic elevational view of a thrombectomy device according to the present invention showing an exemplary configuration in use.

In some examples, the thrombectomy device may be arranged, oriented, or otherwise described relative to a configuration of one or more of the device components. Exemplary configurations of the thrombectomy device may be an approaching configuration, a retracted configuration, an aligned configuration, an expanded configuration, a clot-capture configuration, and a clot-removal configuration. FIG. 4 to FIG. 6 illustrate examples of a thrombectomy device according to the present invention in use within a blood vessel for extraction of thrombus material.

FIG. 4 is an example of a thrombectomy device navigating a blood vessel to a position proximal to a thrombus. The thrombectomy device is illustrated with an optional dilator catheter 405 being advanced through the delivery catheter 410. Also shown is an advancement tool, such as catheter 415 within the delivery catheter 410. The thrombectomy device may comprise imaging elements (e.g., radiopaque elements) 425 coupled to or integrated (e.g., comprising a percentage of volume of an occlusion member 415 materials) with one or more of the thrombectomy device components. The imaging elements can be configured to assist in the navigation, location, placement, position and operation of the thrombectomy device. The occlusion member 416 at the distal end of advancement tool 415 is in a compressed state within the delivery catheter 410. As shown in FIG. 4, the occlusion member 416 is conforming to the interior geometry (e.g., annular) of the delivery catheter 410 prior to being deployed. This view shows in cross-section the filaments 417 of the occlusion member 416.

In some examples, the filaments of an occlusion member may be arranged or adjustable relative to one another based on the configuration of the thrombectomy device (e.g., compressed or expanded). For example, filaments of the occlusion member may be aligned, parallel, perpendicular, intersecting, overlapping, or otherwise oriented relative to one another to facilitate operation of the thrombectomy device.

FIG. 5 is an example of the thrombectomy device positioned in the blood vessel 400 proximal to the thrombus 420. The optional dilator catheter 405 has been partially retracted (e.g., withdrawn) into the catheter 415. The occlusion member 416 is shown in a compressed state within the delivery catheter 410. Imaging elements 425 (e.g., radiopaque elements) may be used to indicate a position of the distal end of the thrombectomy device and/or individual components of the thrombectomy device relative to one another, the vasculature, the thrombus, etc.

In some examples, the (coaxial) arrangement of the catheters (e.g., delivery catheter, occlusion member catheter, dilator catheter) may be configured to increase the column strength and pushability of the thrombectomy device through the vasculature. For example, the dilator catheter extending through the central lumen may increase a column strength of the thrombectomy device and increase navigability within the vasculature.

In FIG. 6, the thrombectomy device is shown in a ready-to-expand configuration with the occlusion member 416 advanced towards the distal end of the delivery catheter 410. The imaging elements 425 indicate an alignment of the distal end of the occlusion member 416 with the distal end of the delivery catheter 410. Distal tip of the thrombectomy device is positioned proximal to the thrombus 420 in preparation for deployment and expansion of the occlusion member.

In some examples, the delivery catheter and/or occlusion member catheter can be controlled or otherwise operationally engaged at their proximal ends. Moving the occlusion member catheter with respect to the delivery catheter, or moving the delivery catheter with respect to the occlusion member catheter, can change the position of the occlusion member with respect to the distal opening of the delivery catheter. In some examples, the occlusion member catheter may have a lumen extending from the distal end to the proximal end allowing a tool (e.g., a clot mobilizer), fluid, etc. to be passed therethrough toward the clot.

Figure 7:
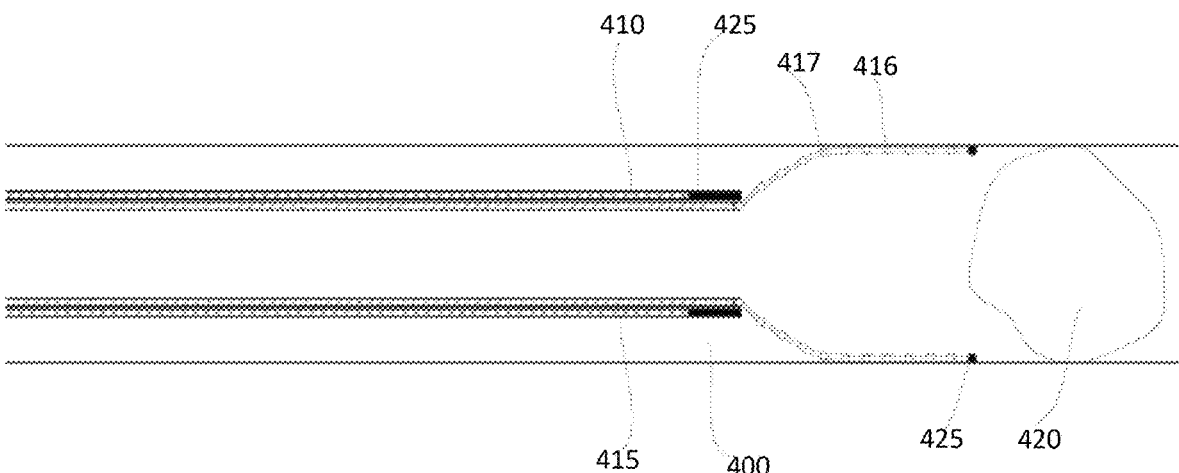
FIG. 7 is a schematic elevational view of a thrombectomy device according to the present invention showing an occlusion member advanced from a delivery catheter in an expanded configuration.

FIG. 7 shows retraction of the delivery catheter 410 to allow the occlusion member 416 to self-expand to its expanded configuration in apposition to inner wall of the vessel 400. In some other examples, the occlusion member may expand to a size (e.g., diameter or cross-sectional area) less than the interior diameter of the blood vessel. The expansion of the occlusion member may be facilitated by the shape-memory material and the configuration (i.e., arrangement) of the filaments of the occlusion member. In this expanded configuration, the thrombus may be extracted from the vessel.

Figure 8:
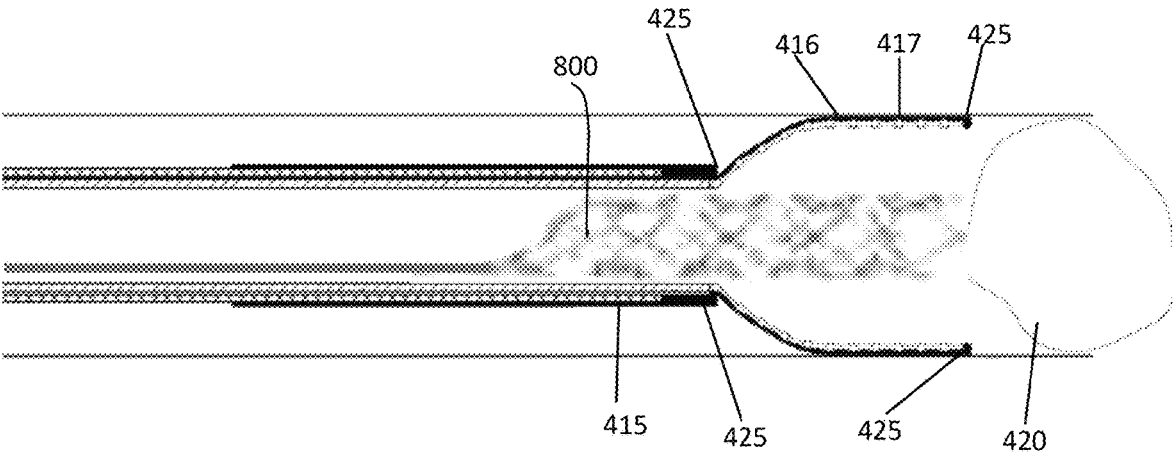
FIG. 8 is a schematic elevational view showing a non-limiting example of a thrombectomy device according to the present invention.

In some examples, the thrombus may be mechanically at least partially into, and retained by, the expanded occlusion member (e.g., expandable funnel). In some examples, suction may be applied to the proximal end of the occlusion member catheter to draw and retain the thrombus at least partially within the expanded occlusion member. In other examples, a mechanical clot-capture element mobilizer may be advanced through the occlusion member catheter and occlusion member to engage and withdraw the clot at least partially into the occlusion member, as shown in FIG. 8. In some examples, a combination of a mechanical clot-capture element (e.g., clot mobilizer) and aspiration may be used to engage and retain the thrombus at least partially within the occlusion member for extraction from the vessel.

FIG. 8 illustrates an example of a clot-capture element 800 extending through the occlusion member catheter and occlusion member 416. In some examples, the clot-capture element may be coupled to a distal end of a pusher wire, or other elongate member configured to advance and retract the clot-capture element. The clot-capture element may be retracted, advanced and deployed with an external micro-catheter. In some examples, aspiration may be supplied via the occlusion member catheter to support the engagement and retention of the thrombus. Clot-capture element 800 is a mere exemplification and a non-limiting example of an auxiliary coaxial device to be used in combination with the thrombectomy device (e.g., occlusion member). The auxiliary device may be a retrieval device (e.g., stent-retriever). The auxiliary device may be a distal access catheter (e.g., distal aspiration catheter). The auxiliary device may be an atherectomy device (e.g., a rotational atherectomy device). The auxiliary device may be a distal protection device. The auxiliary device may be a rheolytic device.

In some examples, one or more elements of the thrombectomy device may comprise one or more materials based on the operation and application of the device for a given procedure. In some examples, the occlusion member may comprise one or more materials configured to transition between a compressed state and an expanded state. In some examples, the occlusion member can be self-expandable. For example, an occlusion member (e.g., expandable funnel) may comprise any material with shape-memory properties (e.g., metals metallic alloys, polymers, ceramics or combination thereof). For example, the occlusion member (e.g., expandable funnel) may comprise Nitinol™ or Nitinol and Platinum, or also Niti #1-DFTR (Drawn Filled Tube), with a percentage of Platinum from 10% to 40%; in particular with 20% Platinum (Niti #1-DFTR-20% Pt) or with 40% Platinum (Niti #1-DFTR-40% Pt). In some examples, the occlusion member is expanded by one or more expansion elements comprised of a material suited to facilitate the expansion and compression (e.g., contraction) of the occlusion member. For example, an expansion member can be the material of the occlusion member, the plurality of closed loops at a distal end, an inflatable element (e.g., balloon) configured to inflate and expand the occlusion member to the interior geometry of the blood vessel. In some examples, the occlusion member is a balloon with an inflatable perimeter and a lumen extending therethrough to the advancement tool.

In some examples, the thrombectomy device (e.g., occlusion member) may comprise a coating suited for expansion, compression, occluding blood flow, directing aspiration, navigating through a blood vessel, etc. In some examples, a thrombectomy device as described herein may comprise a lubricious coating (e.g., hydrophilic, hydrophobic, or a combination thereof).

In some examples, a thrombectomy device according to the present invention can be configured to retrieve a thrombus of any size or dimensions. In some examples, the thrombectomy device may be configured to retrieve a thrombus of any size within a vessel of any diameter. The adaptability of the occlusion member to expand to the interior geometry of a blood vessel allows the occlusion member to be deployed in any vessel. In some examples, the thrombectomy device according to the present invention can be configured to supply an amount of suction, aspiration, vacuum, etc., to retrieve and extract a thrombus, including reversing a flow of blood within the vessel. For example, the occlusion member may be configured to reduce or stop a flow of blood while aspiration may be supplied drawing blood on the other side of the occlusion device. In some examples, the occlusion member may be deployed or used in vasculature with a higher incidence of distal migration, thrombus fracture, mobilization, etc. Accordingly, it may be more advantageous to stop or substantially stop a flow of blood with the occlusion member. For example, narrow vessels may have a higher incidence or potential for clot fragmentation and a thrombectomy device, as described herein, may be adapted to stop a flow of blood thereby reducing or eliminating the potential for clot fragmentation. In some examples, the occlusion member (e.g., expandable funnel) is expandable to the vessel walls so as to adopt the vessel diameter (e.g., from 2.5 mm to 12 mm, more particularly a blood vessel with a diameter between 5 and 6 mm). The occlusion member can be configured to supply aspiration to larger thrombus and with higher vacuum power than other marketed devices (e.g., Navien 0.064", Penumbra 0.072"). For example, a thrombectomy device described herein can include an aspiration funnel catheter composed of a stent covered with a film and a hypotube/catheter (with appropriate connectors at the proximal end) which allows the manipulation of the occlusion member (e.g., expandable funnel) while aspirating the thrombus and during the device removal procedure, thereby reducing the time required to perform the whole thrombectomy intervention.

In some examples, a thrombectomy device may include a small gauge, medium gauge, or large gauge. For example, the gauge may be greater than 0.05 mm, 1 mm, 2 mm, 3 mm, 4 mm, 5 mm, 6 mm, 10 mm, 15 mm, 20 mm, or greater, or any dimension therebetween and without limitation of other sizes according to different needs of device dimensions related to different blood vessel types and diameters. As should be clear the device may have different presentations to fulfill these different needs upon changing the maximum diameter that the occlusion member (e.g., self-expandable funnel) can reach. In any case, once moved outside the delivery catheter, the distal portion of the occlusion member expands to the blood vessel wall. In some examples, to aspirate the thrombus, vacuum is applied through the occlusion member catheter. The said aspiration is exerted with an aspiration device which may be a syringe or aspiration pump at the proximal end of the catheters. The vacuum may be configured to retrieve the thrombus at least partially into the occlusion member.

In some examples, after the thrombus has been captured by the occlusion member, the occlusion member may be retracted at least partially into the delivery catheter (or the delivery catheter may be at least partially advanced over the occlusion member). In some examples, whether or not the occlusion member is at least partially within the delivery catheter, the occlusion member and captured thrombus are retracted proximally through the patient's vasculature and removed from the patient. As the occlusion member moves through the vasculature, the diameters of the blood vessels may increase and decrease along the way. The occlusion member may therefore be configured to conform to any dimensional change of the vessel so as to retain the thrombus therein. In some examples, the occlusion member may narrow proportionally as it lengthens allowing for the thrombus to remain securely within the occlusion member. In some examples, the aspiration catheter (e.g., advancement tool) may be removed from the delivery catheter, and a resheathing element may allow the user to reintroduce (e.g., compress) the occlusion member into the delivery catheter before further use. Such resheathing element can be operably coupled to the delivery catheter. In some examples, the resheathing element can be a modification of the hemostatic valve of the delivery catheter with an appropriate conic closure for closing the aspiration funnel to the diameter of the hemostatic valve. In some examples, the resheathing element is a cannula or funnel with appropriate conical closure and diameter which can be rigid or plastic; if such element has plastic behavior, it can be adjusted to the hemostatic valve diameter and even inserted on its mouth for facilitate the resheathing.

In some examples, the thrombectomy device is configured to be used in combination with one or more automated (e.g., computer-based) systems for navigating vasculature and extracting a thrombus. In some examples, the imaging element (e.g., radiographic markers) can indicate the location of the thrombus, relative position of the thrombectomy device, and coordinate a means of advancing the thrombectomy device within the vasculature to the thrombus for extraction. The thrombectomy device may comprise a control module or communication element in operable communication with a control element engageable by a user for a thrombectomy procedure. The control module may be programmable (e.g., a logic controller, a computer, etc.). In some examples, the control module may be configured to rapid deployment of a thrombectomy device described herein to decrease time to intervention and increase an ease of use during a thrombectomy procedure.

In some examples, a thrombectomy device may be configured to operably couple to a control device. For example, a proximal end of the thrombectomy device may be configured to engage a controller at a proximal end of the thrombectomy device. The controller can be configured to control one or more functions (e.g., deployment, navigation, aspiration, etc.) of the thrombectomy device during use. In some examples, the thrombectomy device may be configured to be rapidly deployed and controlled during a thrombectomy procedure to significantly reduce the time needed to extract a thrombus and recanalize the vasculature for improved patient outcomes. In some examples, the controller may be any controller considered to deploy and navigate an elongate member through a patient's vasculature. In some examples, the controller may be operated manually by a user.

In some examples, the thrombectomy device (e.g., occlusion member) may be used in combination with another auxiliary coaxial device. The auxiliary device may be retrieval device such as a clot mobilizer (e.g., stent retriever). The auxiliary device may be a distal access catheter (e.g., distal aspiration catheter). The auxiliary device may be an atherectomy device (e.g., Rotablator™ rotational atherectomy device). For example, an atherectomy device may be in operable communication with, or used in combination with a thrombectomy device as described herein for the removal of thrombus material or plaque (e.g., atheromatous or calcific plaque) within a vessel. In some examples, the auxiliary device may be a distal protection device. The auxiliary device may be a rheolytic device. The retrieval device or the rheolytic device may be configured to break up (or fragment) the thrombus. When the thrombus is fragmented, aspiration could be applied through the occlusion member. For example, an aspiration device such as AngioJet™ Peripheral Thrombectomy System may be used in combination with the occlusion member.

A method for using a thrombectomy device to extract vascular thrombi can comprise the steps of introducing the thrombectomy device into a blood vessel, guiding the thrombectomy device to a proximal distance from a thrombus, positioning a delivery catheter in a blood vessel target site, deploying an occlusion member, capturing the thrombus at least partially within the occlusion member, and removing the thrombectomy device and thrombus from the blood vessel.

In some examples, the occlusion member expands as it is deployed. The occlusion member may be deployed distally from a distal opening of the delivery catheter by advancing the occlusion member with an advancement tool and/or by retracting the delivery catheter. As the occlusion member is deployed, the distal perimeter of the occlusion member can expand with a radial force outward from a central axis towards the interior of the vessel. In some examples, the distal perimeter of the occlusion member is expanded in apposition to an interior surface of the vessel.

Figure 9:
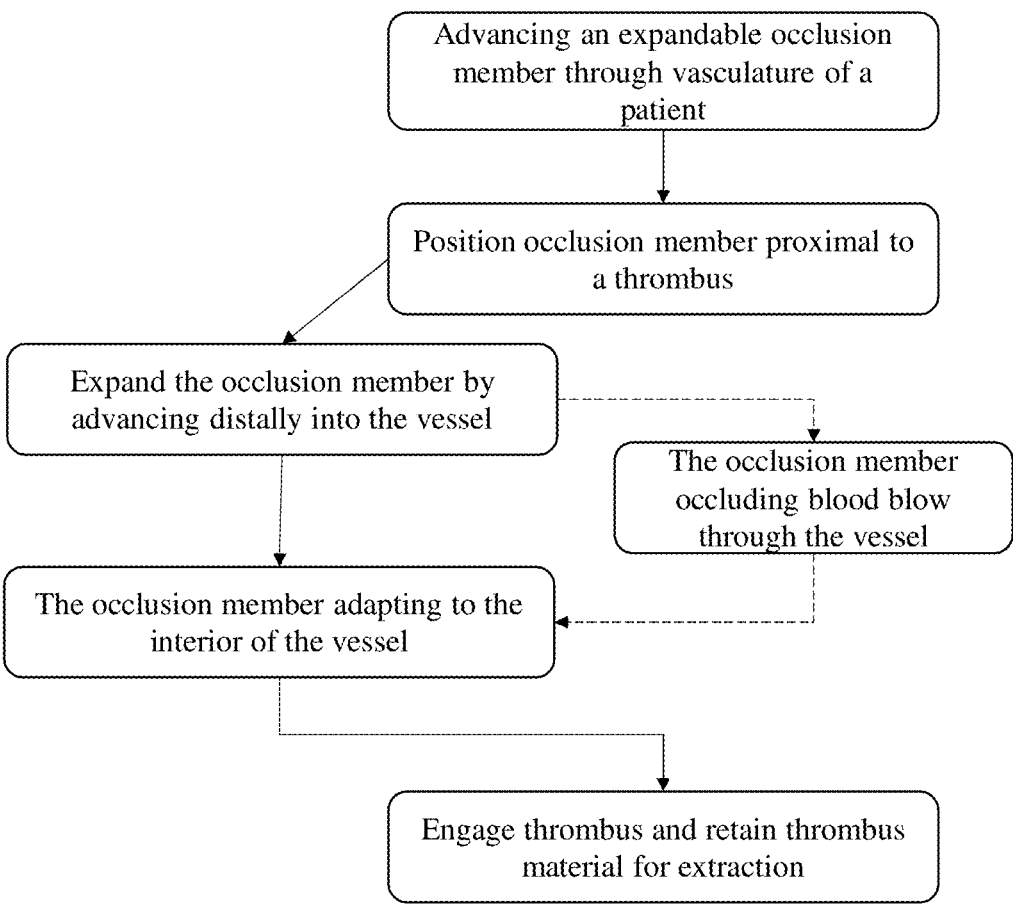
FIG. 9 is a diagram illustrating examples of methods for using a thrombectomy device according to the present invention.

FIG. 9 illustrates a method of extracting a thrombus from a thrombus site in a blood vessel of a patient. After introducing (e.g., inserting) the thrombectomy device, the method can include advancing a delivery catheter and an expandable occlusion member through vasculature of the patient toward the thrombus site. In some examples, the occlusion member is disposed in a retracted (e.g., compressed) position proximal to the distal end of the delivery catheter. Then, the occlusion member and delivery catheter are moved with respect to each other (e.g., advancing the occlusion member distally or retrieving the delivery catheter proximally) to place and deploy the occlusion member in an extended (or expanded) position at least partially outside of the delivery catheter. In some examples, as illustrated in FIG. 9, the method may include a step of occluding the blood vessel with the occlusion member. For example, the occlusion member may be deployed and expanded such that a flow of blood is restricted, reduced, inhibited, occluded, or otherwise decreased by the expansion of the occlusion member. The method may then include moving the thrombus at least partially into the occlusion member. In some examples, the occlusion member captures, engages and retains the thrombus and prevents fragmentation or distal migration of the thrombus material. Finally, the occlusion member and the thrombus are retracted (e.g., withdrawn) proximally within the vasculature. The occlusion member is configured to adapt a shape and length of the occlusion member to a surrounding blood vessel of the vasculature such that the occlusion member lengthens as it narrows to retain the thrombus within the occlusion member as it moves within the blood vessel, for example when the occlusion member is proximally retracted or withdrawn.

In some examples, the occlusion member may be a self-expanding member (e.g., self-expanding funnel) configured to expand to the interior of the vessel. In some examples, expanding the occlusion member may adjust (e.g., decrease) a length of the occlusion member as it expands.

Deploying the occlusion member may include deploying the occlusion member in a straight region of the surrounding vessel (i.e., avoiding improper extension—or expansion—in a tortuous—i.e., curved-region-).

Advancing the occlusion member may include advancing the occlusion member within one or more catheters configure to facilitate navigation through the vasculature. For example, a delivery catheter may be used to house the occlusion member in a compressed state and navigate the vasculature to the thrombus site. In some examples, the delivery catheter may have a deflectable distal segment configured to be selectively deflected to accommodate and navigate through the vasculature. In some examples, the occlusion member within the delivery catheter may be configured to conform to the deflection of the delivery catheter distal segment.

In some examples, the occlusion member is disposed at a distal end of an aspiration catheter. In such embodiments, the method may include an aspirating step that comprises applying vacuum to the occlusion member through the aspiration catheter. In some examples, a vacuum, suction, aspiration, negative pressure, or a combination thereof is supplied to the thrombus and/or the occlusion member.

In some examples, the thrombectomy device may aspirate the thrombus. For example, aspiration may be supplied via the thrombectomy device (e.g., the funnel). A level (e.g., intensity) of aspiration may be selectively controlled during a thrombectomy as needed to aspirate a thrombus within the thrombectomy device. The aspiration or suction may be supplied via a syringe or a suction bomb (or pump).

A thrombectomy device according to the present invention may include a combination of mechanical thrombectomy and aspiration thrombectomy methodologies. One or more configurations of the thrombectomy device including one or more components of the device may be based on the application (e.g., vessel characteristics) where the thrombectomy device will be deployed. For example, in peripheral vessels (e.g., extremities or superior mesenteric arteries) a combination of flow restriction, clot retrieval elements, and/or aspiration can increase first-pass success and prevent clot embolization protection and avoid distal necrosis.

The thrombectomy device described herein may be configured for removal of a thrombus based on the anatomic characteristics of the target vessel and/or thrombus. For example, one or more components comprising a thrombectomy device described herein may be optimally configured to remove a thrombus from a blood vessel based on the size (e.g., diameter) of the target vessel, deployment path to the thrombus location (e.g., vessel tortuosity), the vascular region, the location of the insertion or access point (point where the thrombectomy device is inserted in the body, such as radial access, femoral access or carotid access), vessel condition, thrombus size, thrombus orientation, direction of blood flow in the vessel, and/or pressure of blood flowing through the vessel. Also, any procedure or method of extraction of thrombus from a thrombus site described herein may be selected depending on the target site, vessel anatomy, involved devices, conditions of the flow, location of the insertion point, location of the procedure, among others.

In some examples, the thrombectomy device described herein may include a delivery catheter, an occlusion member and a clot-mobilizer device, such as described, e.g., in U.S. Publ. No. 2022/0117614. In some examples, the clot-mobilizer device may be a stent-retriever device with a closed structure/scaffold and open cells. In some examples, the method described herein may comprise the steps of advancing a microcatheter through vasculature toward the thrombus site, wherein advancing the microcatheter comprises advancing a distal end of the microcatheter through the thrombus, the clot mobilizer device being disposed within the microcatheter; advancing the clot mobilizer until reaching the distal end of the microcatheter, moving the microcatheter and the clot mobilizer device with respect to each other to place the clot mobilizer device outside of the microcatheter allowing the clot mobilizer device to expand from a compressed configuration to an expanded configuration. Particularly, the method further comprises the step of self-expanding the clot mobilizer from the compressed configuration to the expanded configuration. The method described herein may comprise the step of engaging the thrombus with the clot mobilizer device, generating a thrombus-clot mobilizer complex. In some examples, the method described herein may comprise the step of retrieving proximally the clot mobilizer device and the thrombus toward the occlusion member. In some examples, the retrieving step may comprise moving the clot mobilizer device and the thrombus within the occlusion member (and optionally at least partially collapsing the occlusion member) to generate an adhesion of the thrombus and clot mobilizer complex within the occlusion member to avoid fragmenting the thrombus or rolling the thrombus out of the occlusion member. The method described herein may comprise the step of withdrawing the microcatheter outside the body after expanding the clot mobilizer from the compressed configuration to the expanded configuration. The use of a clot-mobilizer with the thrombectomy system may have particular use in the neurovasculature, peripheral arteries and veins, coronary arteries, and renal/abdominal blood vessels. The method described herein may comprise the step of applying aspiration to the occlusion member through the aspiration catheter. In some examples, the clot mobilizer may be configured to improve a suction force due to the generation of adhesion of the thrombus-clot mobilizer complex within the occlusion member by, e.g., reducing the effective opening of the aspiration flow path and/or preventing collapse of the occlusion member due to the aspiration force.

In some examples, the thrombectomy device can be configured to remove a thrombus from the central vascular system or the peripheral vascular system. In some examples, the thrombus is removed from a peripheral blood vessel (e.g., artery or vein) without causing damage to the peripheral blood vessel, avoiding development of additional thrombi, preventing fragmentation, and preventing distal migration. Accordingly, the thrombectomy device described herein can provide increased first pass effect and recanalization. For example, the thrombectomy device may be configured based on a thrombectomy procedure in a region of an extremity (e.g., leg or arm). In some examples, the occlusion member may have specific dimensions or characteristics such as a length, diameter, thickness, elasticity, texture, shape, etc. (e.g., as in FIGS. 2A and 2B) configured to capture, engage and/or retain a thrombus from a peripheral blood vessel. In some examples, the occlusion member is configured to exert a specific outward radial force to the vessel, due to the specific dimensions (e.g., diameter, length, and/or shape). In some examples, the thrombus site is in a peripheral artery. The peripheral artery may be a renal artery, a mesenteric artery, a femoral artery, a popliteal artery, a tibial artery, a vertebral vessel, a perineal artery, a hepatic artery, an iliac artery, or a splenic artery. The step of moving the thrombus may comprise aspirating the thrombus into the occlusion member.

In some examples, the thrombectomy device can be configured to remove a thrombus from a coronary blood vessel (e.g., artery or vein) without causing damage to the coronary blood vessel, avoiding development of additional thrombi, preventing fragmentation, preventing distal migration, and preventing coronary vessel spasms. Accordingly, the thrombectomy device described herein can provide increased first pass effect and recanalization. In some examples, the occlusion member may have a length, diameter and shape (e.g., as in FIG. 2B) based on the vessel characteristics and the occlusion member can be configured to capture, engage and/or retain a thrombus from a coronary blood vessel. In some examples, the occlusion member may have a first diameter near or between 3 and 4 millimeters (both inclusive) at its distal end and a second diameter near or between 1.5 and 2 millimeters (both inclusive) at its proximal end. In some examples, the occlusion member is configured to exert a specific outward radial force to the vessel, due to the specific diameter, length, and/or shape.

In some examples, the thrombectomy device can be configured to remove a thrombus from a pulmonary blood vessel (e.g., artery or vein) without causing damage to the pulmonary blood vessel, avoiding development of additional thrombi, preventing fragmentation (unless fragmentation of the thrombus is desired, such as while treating pulmonary emboli or deep vein thrombosis), and preventing distal migration. Accordingly, the thrombectomy device described herein can provide increased first pass effect and recanalization. In some examples, the occlusion member may have a specific length, diameter and shape (e.g., as in FIGS. 2A and 2B) configured to capture, engage and/or retain a thrombus from a pulmonary blood vessel. In some examples, the occlusion member may have a first diameter near 8 millimeters at its distal end and a second diameter near 6 mm at its proximal end. In some examples, the occlusion member is configured to exert a specific outward radial force to the vessel, due to the specific diameter, length, and/or shape.

In some examples, the thrombectomy device can be configured to remove a thrombus from a vertebral vessel (e.g., artery or vein) without causing damage to the vertebral vessel, avoiding development of additional thrombi, preventing fragmentation, and preventing distal migration. Accordingly, the thrombectomy device described herein can provide increased first pass effect and recanalization.

In some examples, the thrombectomy device can be configured to remove a thrombus from an intracranial blood vessel (e.g., artery or vein) without causing damage to the intracranial blood vessel, avoiding development of additional thrombi, preventing fragmentation, and preventing distal migration. The thrombectomy device described herein can provide increased first pass effect and recanalization. For examples, an occlusion site is in the cerebral vasculature, and the thrombectomy device can be configured to navigate to and operate in the internal carotid artery at or proximal to the distal end of the carotid siphon (e.g., in or near the apex of the carotid siphon), or even proximal to the proximal end of the carotid siphon. This may include advancing a clot-mobilizer and/or a distal access catheter further distally to the occlusion site in the cerebral vasculature beyond the carotid siphon to capture and retrieve the thrombus. In some examples, the occlusion member may have dimensions tailored to a thrombus site, occlusion site, path of advancement through the vasculature, etc. or a combination thereof. For example, an occlusion member may have a specific length, diameter and shape (e.g., as in FIGS. 2A and 2B) configured to capture, engage and/or retain a thrombus from an intracranial blood vessel. In some examples, the occlusion member may have a first diameter near or between 5 and 7 millimeters (both inclusive) at its distal end and a second diameter near or between 1.5 and 2.5 millimeters (both inclusive) at its proximal end. In some examples, the occlusion member is configured to exert a specific outward radial force to the vessel, due to the specific diameter, length, and/or shape.

In some examples, the thrombectomy device can be configured to remove a thrombus from the iliac artery without causing damage to the blood vessel, avoiding development of additional thrombi, preventing fragmentation, and preventing distal migration. The thrombectomy device described herein can provide increased first pass effect and recanalization. For examples, an occlusion site is in the iliac artery, and the thrombectomy device can be configured to navigate to and operate in and through the peripheral vasculature at or proximal to the distal end of thrombus. This may include advancing a clot-mobilizer and/or a distal access catheter further distally to the occlusion site in the iliac artery to capture and retrieve the thrombus. In some examples, the occlusion member may have dimensions tailored to a thrombus site, occlusion site, path of advancement through the vasculature, etc. or a combination thereof. For example, an occlusion member may have a specific length, diameter and shape (e.g., as in FIGS. 2A and 2B) configured to capture, engage and/or retain a thrombus from an intracranial blood vessel. In some examples, the occlusion member may have a first diameter near or between 9 and 12 millimeters (both inclusive) at one or more segments or sections. In some examples, the occlusion member may expand from a first diameter to a diameter between 9 and 12 millimeters. In some examples, the occlusion member is configured to exert a specific outward radial force to the vessel, due to the specific diameter, length, and/or shape.

In some examples, the thrombectomy device can be configured to remove a thrombus from the hepatic artery without causing damage to the blood vessel, avoiding development of additional thrombi, preventing fragmentation, and preventing distal migration. The thrombectomy device described herein can provide increased first pass effect and recanalization. For example, an occlusion site is in the hepatic artery, and the thrombectomy device can be configured to navigate to and operate in and through the peripheral vasculature at or proximal to the distal end of thrombus. This may include advancing a clot-mobilizer and/or a distal access catheter further distally to the occlusion site in the hepatic artery to capture and retrieve the thrombus. In some examples, the occlusion member may have dimensions tailored to a thrombus site, occlusion site, path of advancement through the vasculature, etc. or a combination thereof. For example, an occlusion member may have a specific length, diameter and shape (e.g., as in FIGS. 2A and 2B) configured to capture, engage and/or retain a thrombus from an intracranial blood vessel. In some examples, the occlusion member may have a first diameter near or between 10 and 14 millimeters (both inclusive) at one or more segments or sections. In some examples, the occlusion member may expand from a first diameter to a diameter between 10 and 14 millimeters. In some examples, the occlusion member is configured to exert a specific outward radial force to the vessel, due to the specific diameter, length, and/or shape.

In some examples, one or more diameters of the occlusion member may be or may be expanded to include between 5 millimeters and 6 millimeters (e.g., at or near 5.2 millimeters). In some examples, one or more diameters of the occlusion member may be or may be expanded to include between 6 millimeters and 7 millimeters (e.g., at or near 6.6 millimeters).

In some examples, the thrombectomy device can be configured to remove a thrombus from a blood vessel (e.g., artery or vein) associated with the abdomen, trunk, or thorax without causing damage to the blood vessel, avoiding development of additional thrombi, preventing fragmentation, and preventing distal migration. Accordingly, the thrombectomy device described herein can provide increased first pass effect and recanalization.

In some examples, the thrombectomy device can be configured to remove a thrombus from a blood vessel affected by deep-venous thrombosis without causing damage to the blood vessel, avoiding development of additional thrombi, preventing fragmentation (once again, unless fragmentation is desired), and preventing distal migration. Accordingly, the herein can provide increased first pass effect and recanalization. thrombectomy device described herein can provide increased first pass effect and recanalization.

While exemplary thrombectomy device configurations provided herein may be particularly suited for removal of thrombi from one or more regions of an anatomy, any of the devices may be used to remove a thrombus in any vessel (e.g., any artery or any vein). For example, a thrombectomy device described herein may be particularly suited for the removal of a thrombus from the abdominal aorta, anterior descending artery, anterior tibial artery, aorta, arteria dorsalis pedis, axillary artery, brachial artery, brachiocephalic artery, bronchial arteries, celiac artery, circumflex artery, common carotid artery, common hepatic artery, common iliac arteries, coronary artery, costocervical trunk, descending aorta, dorsal scapular artery, dorsalis pedis artery, external carotid artery, external iliac artery, femoral artery, gastric artery, hypogastric artery, inferior mesenteric artery, internal carotid artery, internal iliac artery, internal thoracic artery, intracranial arteries, peroneal artery, popliteal artery, posterior tibial artery, profunda femoris artery, pulmonary artery, radial artery, renal arteries, splenic artery, subclavian artery, superior mesenteric artery, thoracic aorta, thyrocervical trunk, triangles of the neck, ulnar artery, vertebral artery, or any vessel associated therewith. For example, a thrombectomy device described herein may be particularly suited for the removal of a thrombus from the internal jugular vein, external jugular vein, anterior jugular vein, subclavian vein, brachiocephalic veins, superior vena cava, azygos vein, hemiazygos vein, iliac veins, inferior vena cava, basilic vein, cephalic vein, radial vein, ulnar vein, brachial vein, axillary veins, anterior tibial vein, posterior tibial vein, fibular/peroneal vein, popliteal vein, femoral vein, great saphenous vein, small saphenous vein, external iliac vein, common iliac veins, or any vessel associated therewith.

There may be one or more variations, alternatives, constructions, compositions, and/or components described herein that can be used to modify an element, component, device, system, process, etc. of a guide element, intravascular access device and/or an associated structure or process. Accordingly, any variation, description, example, element, component, process, method, method step, etc. described herein can be used as a modification, variation, and/or alternative to any element, device, system, composition, example, component, process, method, method step, etc. described in U.S. Publ. No. 2021/0236150, U.S. Publ. No. 2022/0000500, or U.S. Publ. No. 2022/0117614, the entireties of which are incorporated herein.

While certain features and embodiments of the invention have been shown and described, many modifications and changes may occur to those skilled in the art (e.g., variations in sizes, dimensions, structures, shapes and proportions of the various elements, values of parameters (e.g., temperatures, pressures, etc.), mounting arrangements, use of materials, colors, orientations, etc.) without materially departing from the novel teachings and advantages of the subject matter recited in the claims. The order or sequence of any process or method steps may be varied or re-sequenced according to alternative embodiments.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A thrombectomy device comprising:
a delivery catheter; and
an expandable occlusion member configured to be movably disposed within the delivery catheter in a retracted position and at least partially outside the delivery catheter in an extended position, the occlusion member comprising a non-permeable covering, a diameter of a distal end of the occlusion member being greater in the extended position than in the retracted position, the occlusion member in its extended position being configured to adapt its shape and length to a surrounding blood vessel such that the occlusion member expands to a diameter of the blood vessel and occludes the blood vessel and such that the occlusion member lengthens as it narrows to retain a thrombus within the occlusion member during movement of the occlusion member through the blood vessel.

2. The thrombectomy device of claim 1, further comprising a tapered dilator catheter configured to be movably disposed within the delivery catheter, wherein the occlusion member is configured to remain within the delivery catheter after the dilator catheter has been removed.

3. The thrombectomy device of claim 2, wherein the delivery catheter, dilator catheter and occlusion member are oriented on the same axis.

4. The thrombectomy device of claim 1, wherein the occlusion member is self-expandable.

5. The thrombectomy device of claim 1, wherein the occlusion member comprises a shape memory material.

6. The thrombectomy device of claim 5, wherein the shape memory material comprises nitinol.

7. The thrombectomy device of claim 1, wherein the occlusion member has a diameter at its distal end of between 2 millimeters and 15 millimeters.

8. The thrombectomy device of claim 1, wherein the delivery catheter and occlusion member are oriented on the same axis.

9. The thrombectomy device of claim 1, further comprising a resheathing element adapted to reintroduce the occlusion into the delivery catheter, the resheathing element comprising a cannula, a clamp, a funnel, or any combination of them.

10. The thrombectomy device of claim 1, further comprising an aspiration catheter comprising the occlusion member and a tube extending proximally from a proximal opening of the occlusion member, the aspiration catheter being configured to aspirate and capture the thrombus.

11. The thrombectomy device of claim 1, wherein the delivery catheter is configured to deliver the occlusion member to a vascular artery.

12. The thrombectomy device of claim 11, wherein the vascular artery is a coronary artery.

13. The thrombectomy device of claim 11, wherein the vascular artery is a pulmonary artery.

14. The thrombectomy device of claim 11, wherein the vascular artery is a peripheral artery.

15. The thrombectomy device of claim 14, wherein the peripheral artery is a renal artery, a mesenteric artery, a femoral artery, a popliteal artery, a tibial artery, vertebral artery, a perineal artery, a hepatic artery, a splenic artery, or an iliac artery.

16. The thrombectomy device of claim 1, wherein the delivery catheter is configured to deliver the occlusion member to a vein.

17. The thrombectomy device of claim 16, wherein the vein is a peripheral vascular system vein.

18. The thrombectomy device of claim 16, wherein the vein is a central vascular system vein.

19. The thrombectomy device of claim 1, wherein the expandable occlusion member comprises an expandable funnel.

20. A system for extraction of vascular thrombi from a blood vessel comprising the thrombectomy device of claim 1, wherein the system further comprises a communications channel, a control module, a data storage device, and a guidance system, wherein the control module is guided by a computer-assisted controller.

* * * * *